(12) United States Patent
Majumdar

(10) Patent No.: US 10,777,303 B2
(45) Date of Patent: Sep. 15, 2020

(54) TOOL FOR VISUALIZING PCR RESULTS

(71) Applicant: LIFE TECHNOLOGIES CORPORATION, Carlsbad, CA (US)

(72) Inventor: Nivedita Sumi Majumdar, San Bruno, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 68 days.

(21) Appl. No.: 15/745,218

(22) PCT Filed: Jul. 15, 2016

(86) PCT No.: PCT/US2016/042553
§ 371 (c)(1),
(2) Date: Jan. 16, 2018

(87) PCT Pub. No.: WO2017/015133
PCT Pub. Date: Jan. 26, 2017

(65) Prior Publication Data
US 2018/0225415 A1 Aug. 9, 2018

Related U.S. Application Data

(60) Provisional application No. 62/194,055, filed on Jul. 17, 2015.

(51) Int. Cl.
*G06F 3/0481* (2013.01)
*G06T 11/20* (2006.01)
*G16B 45/00* (2019.01)

(52) U.S. Cl.
CPC .......... *G16B 45/00* (2019.02); *G06F 3/0481* (2013.01); *G06T 11/206* (2013.01)

(58) Field of Classification Search
CPC ...... G16B 45/00; G06F 3/0481; G06T 11/206
USPC .......................................................... 715/771
See application file for complete search history.

(56) References Cited

U.S. PATENT DOCUMENTS

2011/0252353 A1* 10/2011 Janaway ............... G06F 3/0482
715/771

FOREIGN PATENT DOCUMENTS

WO 2014074735 A2 5/2014

OTHER PUBLICATIONS

International Preliminary Report on Patentability and Written Opinion issued in International Application No. PCT/US2016/042553 dated Jan. 23, 2018.

* cited by examiner

*Primary Examiner* — Tadesse Hailu
*Assistant Examiner* — Darrin Hope
(74) *Attorney, Agent, or Firm* — Jones Robb, PLLC

(57) ABSTRACT

In some embodiments, a method or system for visualizing data generated from one or more reaction devices, chips, or reaction sites may be provided. On a scatter plot, data points may be displayed indicative of results from nucleic amplification, wherein the nucleic acid amplification comprises a first target and a second target and the data points are designated as being indicative of amplification of the first target, the second target, both targets, or neither target. In response to user input, an adjustable threshold may be varied used to designate the data points. And, in response to the varying, designations and a display of the designations may be altered for one or more of the data points whose designation is changed based on the varied threshold.

20 Claims, 25 Drawing Sheets

FIG. 15

TOOL FOR VISUALIZING PCR RESULTS

This application is a U.S. national stage application under 35 U.S.C. § 371(c) of International Application No. PCT/US2016/042553, which claims the benefit of priority of U.S. Provisional Application No. 62/194,055, filed Jul. 17, 2015, each of which is incorporated by reference herein in its entirety.

BACKGROUND

Systems for biological and biochemical reactions have been used to monitor, measure, and/or analyze such reactions in real time. Such systems are commonly used in sequencing, genotyping, polymerase chain reaction (PCR), and other biochemical reactions to monitor the progress and provide quantitative data.

Currently, there is an increasing demand to provide greater numbers of reactions per test or experiment have resulted in instruments that are able to conduct ever higher numbers of reactions simultaneously. The increase in the number sample sites in a test or experiment has led to microtiter plates and other sample formats that provide ever smaller sample volumes. In addition, techniques such as digital PCR (dPCR) have increased the demand for smaller sample volumes that contain either zero or one target nucleotide sequence in all or the majority of a large number of test samples.

Digital PCR may be used to detect and quantify the concentration of rare alleles, to provide absolute quantitation of nucleic acid samples, and to measure low fold-changes in nucleic acid concentration. Increasing the partitions for the dPCR reaction may increase the accuracy and reproducibility of dPCR results.

In dPCR, a solution containing a relatively small number of a target polynucleotide or nucleotide sequence may be subdivided into a large number of small test samples, such that each sample generally contains either one or more molecule(s) of the target nucleotide sequence or none of the target nucleotide sequence. When the samples are subsequently thermally cycled in a PCR protocol, procedure, or experiment, the samples containing the target nucleotide sequence are amplified and produce a positive detection signal, while the samples containing no target nucleotide sequence are not amplified and produce no detection signal.

For further analysis, the data collected from a dPCR experiment is challenging to analyze and visualize in a manner that is useful to a user, and is further challenging to quantify, in particular when dealing with rare occurrences.

SUMMARY

In some embodiments, a method or system for visualizing data generated from one or more reaction devices, chips, or reaction sites, may be presented. On a scatter plot, data points may be displayed indicative of results from nucleic amplification, wherein the nucleic acid amplification comprises a first target and a second target and the data points are designated as being indicative of amplification of the first target, the second target, both targets, or neither target. In response to user input, an adjustable threshold may be varied used to designate the data points. And, in response to the varying, designations and a display of the designations may be altered for one or more of the data points whose designation is changed based on the varied threshold.

DESCRIPTION OF THE FIGURES

FIG. 15 illustrates a graphical user interface that displays a dashboard for configuring a rare mutation analysis according to various embodiments.

DETAILED DESCRIPTION

The following description sets forth numerous specific details, such as specific configurations, parameters, examples, and the like. It should be recognized, however, that such description is not intended as a limitation on the scope of the disclosed embodiments, but is intended to provide a better description of these embodiments.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

Figure 1:
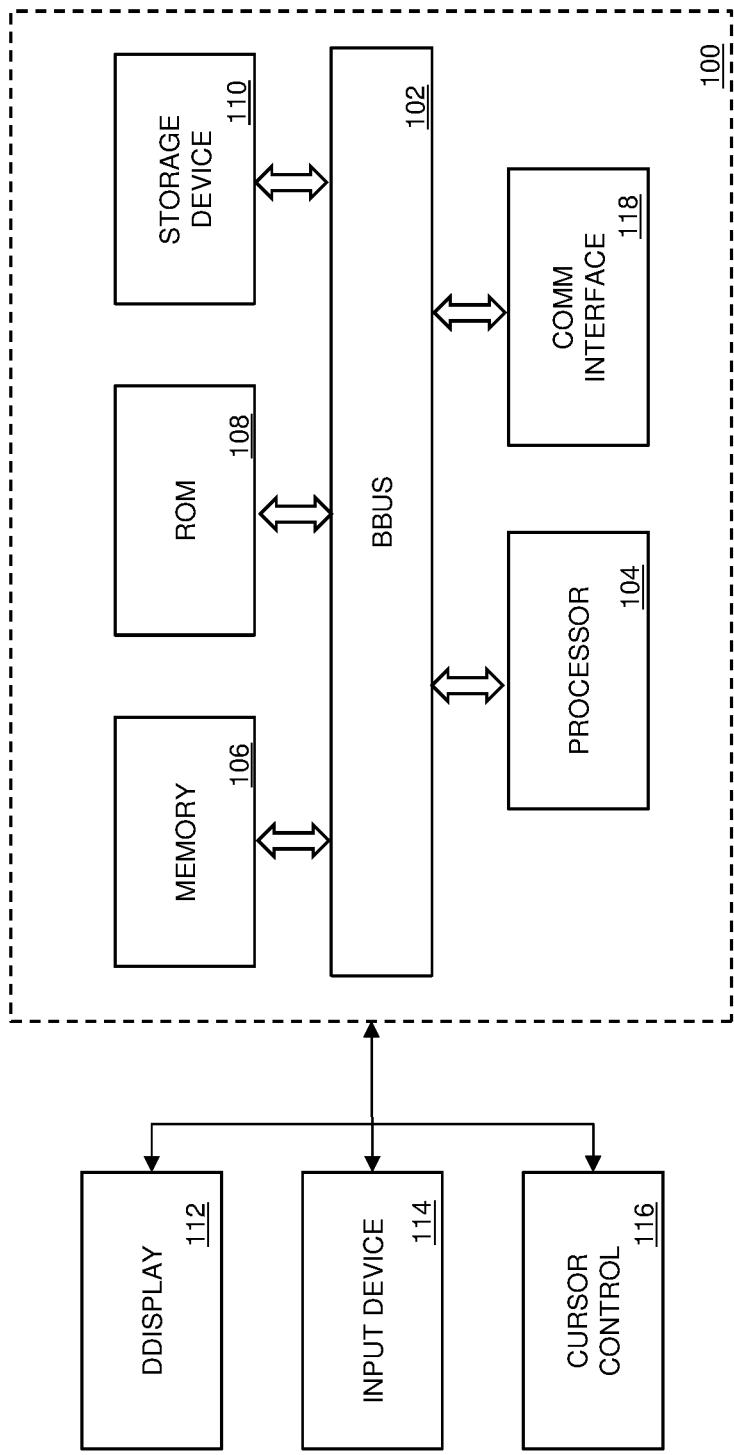
FIG. 1 illustrates an exemplary computing system that various embodiments described herein may be implemented.

FIG. 1 is a block diagram that illustrates a computer system 100 that may be employed to carry out processing functionality, according to various. Computing system 100 can include one or more processors, such as a processor 104. Processor 104 can be implemented using a general or special purpose processing engine such as, for example, a microprocessor, controller or other control logic. In this example, processor 104 is connected to a bus 102 or other communication medium.

Further, it should be appreciated that a computing system 100 of FIG. 1 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 100 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 100 may include bus 102 or other communication mechanism for communicating information, and processor 104 coupled with bus 102 for processing information. Computing system 100 also includes a memory 106, which can be a random access memory (RAM) or other dynamic memory, coupled to bus 102 for storing instructions to be executed by processor 104. Memory 106 also may be used for storing temporary variables or other intermediate information during execution of instructions to be executed by processor 104. Computing system 100 further includes a read only memory (ROM) 108 or other static storage device coupled to bus 102 for storing static information and instructions for processor 104.

Computing system 100 may also include a storage device 110, such as a magnetic disk, optical disk, or solid state drive (SSD) is provided and coupled to bus 102 for storing information and instructions. Storage device 110 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 110 may include other similar instrumentalities for allowing computer programs or other instructions or data to be loaded into computing system 100. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 110 to computing system 100.

Computing system 100 can also include a communications interface 118. Communications interface 118 can be used to allow software and data to be transferred between computing system 100 and external devices. Examples of communications interface 118 can include a modem, a network interface (such as an Ethernet or other NIC card), a communications port (such as for example, a USB port, a RS-232C serial port), a PCMCIA slot and card, Bluetooth, etc. Software and data transferred via communications interface 118 may be in the form of signals which can be electronic, electromagnetic, optical, or other signals capable of being received by communications interface 118. These signals may be transmitted and received by communications interface 118 via a channel such as a wireless medium, wire or cable, fiber optics, or other communications medium. Some examples of a channel include a phone line, a cellular phone link, an RF link, a network interface, a local or wide area network, and other communications channels.

Computing system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104, for example. An input device may also be a display, such as an LCD display, configured with touchscreen input capabilities. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane. A computing system 100 provides data processing and provides a level of confidence for such data. Consistent with certain implementations of embodiments of the present teachings, data processing and confidence values are provided by computing system 100 in response to processor 104 executing one or more sequences of one or more instructions contained in memory 106. Such instructions may be read into memory 106 from another computer-readable medium, such as storage device 110. Execution of the sequences of instructions contained in memory 106 may cause processor 104 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 104 for execution.

Such instructions, generally referred to as "computer program code" (which may be grouped in the form of computer programs or other groupings), when executed, enable the computing system 100 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 104 for execution. For example, the instructions may initially be carried on magnetic disk of a remote computer. The remote computer can load the instructions into its dynamic memory and send the instructions over a telephone line using a modem. A modem local to computing system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

It will be appreciated that, for clarity purposes, the above description has described embodiments with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

In various embodiments, the devices, instruments, systems, and methods described herein may be used to detect one or more types of biological components of interest. These biological components of interest may be any suitable biological target including, but are not limited to, DNA sequences (including cell-free DNA), RNA sequences, genes, oligonucleotides, molecules, proteins, biomarkers, cells (e.g., circulating tumor cells), or any other suitable target biomolecule.

In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation. Embodiments of the present disclosure are generally directed to devices, instruments, systems, and methods for monitoring or measuring a biological reaction for a large number of small volume samples. As used herein, samples may be referred to as sample volumes, or reactions volumes, for example.

While applicable to quantitative polymerase chain reactions (qPCR) where a large number of samples are being processed, it should be recognized that any suitable PCR method may be used in accordance with various embodiments described herein. Suitable PCR methods include, but are not limited to, digital PCR, allele-specific PCR, asymmetric PCR, ligation-mediated PCR, multiplex PCR, nested PCR, qPCR, genome walking, and bridge PCR, for example.

As described below, in accordance with various embodiments described herein, reaction sites may include, but are not limited to, through-holes, wells, microwells, indentations, spots, cavities, sample retainment regions, and reaction chambers, for example.

Furthermore, as used herein, thermal cycling may include using, for example, a thermal cycler, isothermal amplification, thermal convention, infrared mediated thermal cycling, or helicase dependent amplification. In some embodiments, the chip may be integrated with a built-in heating element. In various embodiments, the chip may be integrated with semiconductors.

According to various embodiments, detection of a target may be, but is not limited to, fluorescence detection, detection of positive or negative ions, pH detection, voltage detection, or current detection, alone or in combination, for example.

Various embodiments outlined within this disclosure may implement dPCR amplification. In dPCR, and other "digital" amplification techniques, a sample may be partitioned so that a small amount of nucleic acid molecules within the sample are localized and concentrated within many separate reaction volumes. A reaction volume may comprise a volume of liquid, for example 1 μL or any other suitable volume, that comprises reagents for amplification, such as PCR amplification. The reagents may include one or more target nucleic acids and reagents of an amplification assays (e.g., probes, primers, dyes, and the like). Reaction volumes may be segregated among wells, microwells, through-holes, droplets, or any other suitable segregation configuration. In some examples, the sample is partitioned by a dilution process such that each sample portion in a reaction volume contains either approximately one copy of nucleic acid template (target) or no copy of the nucleic acid template (target). Similar to PCR, dPCR may progress by exposing the partitioned sample reaction volumes, which contain reagents for amplification, to an amplification assay designed to amplify the target nucleic acid. For example, thermal cycling may be performed such that the template nucleic acid is amplified within the reaction chambers that include an initial approximately one copy of the template nucleic acid molecule.

In order to quantify the nucleic acid amplification, an indicator of amplification exhibited by the reaction volumes may be detected. In some exemplary embodiments in accordance with the present disclosure, one or more fluorescent dyes may be used such that the dyes bond to nucleic acids and exhibit fluorescence to indicate presence of a nucleic acid.

For example, amplified target nucleic acids can be detected using a detectable nucleic acid binding agent which can be, for example, an intercalating agent or a non-intercalating agent. As used herein, an intercalating agent is an agent or moiety capable of non-covalent insertion between stacked base pairs of a double-stranded nucleic acid molecule. A non-intercalating agent is one that does not insert into the double-stranded nucleic acid molecule. The nucleic acid binding agent can produce a detectable signal directly or indirectly. The signal can be detectable directly using, for example, fluorescence or absorbance, or indirectly using, for example, any moiety or ligand that is detectably affected by its proximity to double-stranded nucleic acid is suitable, for example a substituted label moiety or binding ligand attached to the nucleic acid binding agent. It is typical for the nucleic acid binding agent to produce a detectable signal when bound to a double-stranded nucleic acid that is distinguishable from the signal produced when that same agent is in solution or bound to a single-stranded nucleic acid. For example, intercalating agents such as ethidium bromide fluoresce more intensely when intercalated into double-stranded DNA than when bound to single-stranded DNA, RNA, or in solution (see, e.g., U.S. Pat. Nos. 5,994,056; 6,171,785; and 6,814,934). Similarly, actinomycin D fluoresces red when bound to single-stranded nucleic acids, and green when bound to double-stranded nucleic acids.

Non-intercalating agents (e.g., minor groove binders such as Hoechst 33258, distamycin, netropsin) may also be suitable for use. For example, Hoechst 33258 (Searle, et al. Nucleic Acids Res. 18:3753-3762 (1990)) exhibits altered fluorescence with an increasing amount of target. SYBR® Green I (see, e.g., U.S. Pat. Nos. 5,436,134; 5,658,751; and/or 6,569,927), for example, has been used to monitor an amplification (e.g., PCR) reaction by amplifying the target sequence in the presence of the dye, exciting the biological sample with light at a wavelength absorbed by the dye and detecting the emission therefrom. It is to be understood that the use of the SYBR® Green dye is presented as an example and that many such dyes may be used in the methods described herein. Other nucleic acid binding agents can also be suitable as would be understood by one of skill in the art.

In order to conduct a typical dPCR protocol, procedure, or experiment, it is advantageous to be able to divide an initial sample solution into tens of thousands or hundreds of thousands of test samples each having a volume of several nanoliters, at or about one nanoliter, or less than one nanoliter, in a way that is simple and cost effective.

Figure 2:
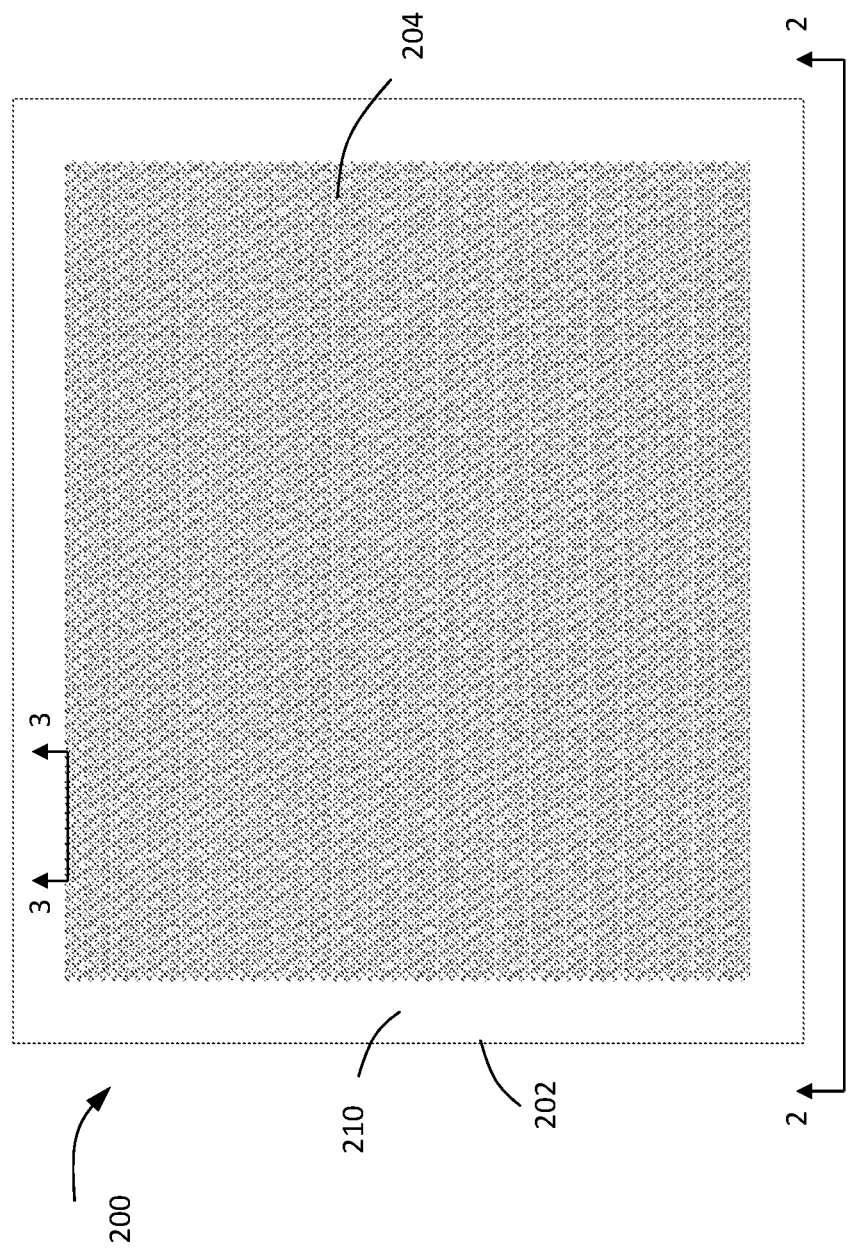
FIG. 2 illustrates a chip including reaction sites where data is gathered from and visualized according to various embodiments.

In various embodiments, the devices, instruments, systems, and methods described herein may be used to detect one or more types of biological components of interest. These biological components of interest may include, but are not limited to, DNA sequences, RNA sequences, genes, oligonucleotides, or cells (e.g., circulating tumor cells). In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation. With reference to FIG. 2, in certain embodiments of the present teachings a chip 200 comprises a substrate 202 and a plurality of reaction sites 204. Chip 200 may also be referred to as an article, device, array, slide, or platen, for example. In some examples, chip 200 may comprise a QuantStudio™ 3 D chip.

According to various embodiments of the present disclosure, reaction sites 204 may be, but are not limited to, wells, microwells, cavities, indentations, spots, reaction chambers, sample retainment regions, or through-holes, for example, located in substrate 202. Reaction sites may be any structure that allows a sample to be independent of other samples located on the substrate. Substrate 202 comprises a first surface 210 and an opposing second surface (not pictured).

Substrate 202 may be a flat plate or comprise any form suitable for a particular application or design. Substrate may comprise, in total or in part, any of the various materials known in the fabrication arts including, but not limited to, a metal, glass, ceramic, silicon material, or the like. Additionally or alternatively, substrate 202 may comprise a polymer material such as an acrylic, styrene, polyethylene, polycarbonate, and polypropylene material. Substrate 202 and reaction sites 204 may be formed by one or more of machining, injection molding, hot embossing, laser drilling, photolithography, or the like.

The reactions sites 204 are configured to provide sufficient surface tension by capillary action to hold respective liquid samples containing a biological sample to be processed or examined.

In various described embodiments, chip 200 may be used for performing PCR (e.g., dPCR or qPCR). The amplification techniques described herein may be performed with a sample chip, a circuit board, a TLDA card, droplets in a free solution, droplets on a planar surface, droplets over a temperature gradient, droplets in capillary tubes or flow systems, microfluidic device with individual chambers, 384-well plate, higher well plate, array of reaction wells, or with any other suitable device and/or detection technique for dPCR with which those having ordinary skill in the art are familiar. Various exemplary devices may also be utilized to implement the PCR detection methods described herein.

An initial step in the amplification process may comprise loading a sample such that the sample is segregated into a plurality of sample reaction volumes. For instance, loading may comprise segregating the reaction volumes among the reaction sites 204 of chip 200. In some examples that implement digital amplification, a first plurality of the sample reaction volumes may contain at least one molecule of a target nucleic acid and a second plurality of the sample reaction volumes contain no molecules of the target nucleic acid. The sample may be fractionated by a dilution process so that each sample reaction volume contains approximately one copy of the target nucleic acid or contains no copy of the target nucleic acid. In an embodiment, the segregated sample reaction volumes may include a plurality of reagents for amplifying the target nucleic acid molecules. The reagents may be incorporated into the sample prior to segregation or after segregation.

Next, the plurality of sample reaction volumes may be subjected to an amplification assay. For example, the plurality of sample reaction volumes may be simultaneously subjected to an amplification assay, wherein the amplification assay is designed to amplify the target nucleic acid to produce amplified product (i.e., one or more amplicons). The assay may utilize at least a primer, probe and/or dye, and an enzyme, such as a Taqman™ assay or any other suitable assay, as those having ordinary skill in the art are familiar with. Accordingly, the sample reaction volumes contain the sample portion and the reagents for amplification and detection.

In some embodiments, an assay may include two probes, such as a FAM™ dye-labeled probe and a VIC® dye-labeled probe, and amplification detection results based on each dye may be utilized in order to determine quantities for amplified target nucleic acid(s). For instance, multiple indicators of amplification may be exhibited from a sample reaction volume based on each of the dye-labeled probes. An assay may also include a variety of primers, such as ELITe® primers. In an embodiment, one ELITe® primer may overlap a target sequence (i.e., an allele specific primer) while one ELITe® primer may not (i.e., a locus specific primer). Some implementations may leverage a standard primer rather than an ELITe® primer for the locus specific primer. In some embodiments, a multiplexing assay may be used where multiple allele specific primers may generate amplicons with a single locus specific primer.

In some embodiments, an assay may include primers designed to identify amplification reactions involving normal (wild-type) nucleic acids and non-normal (rare) nucleic acids. An assay may also include primers designed to identify certain types of mutations (i.e., single nucleotide polymorphisms (SNPs) and inDels at locus within amplicons). In some embodiments, use of known spike-in concentrations may also be leveraged for identification. Various embodiments may utilize ELITe® primers, non-ELITe® (standard) primers, or any suitable combination.

In an exemplary embodiment, the plurality of sample reaction volumes subjected to the amplification assay may be further subjected to a plurality of PCR steps, such as thermal cycling, as described herein. For example, a temperature of the sample reaction volumes may be increased to physically separate strands of the target nucleic acid (i.e. strands of a nucleic acid molecule). The temperature may then be decreased and each strand may be used as a template for synthesis by an enzyme (i.e., polymerase) to selectively amplify the target nucleic acid, for instance during annealing and extension phases of the PCR process. In an embodiment, a plurality of PCR cycles may be performed that result in amplification of the target nucleic acid molecule.

After or during amplification, results for an indicator of amplification product presented by the plurality of sample reaction volumes may be detected. For example, an indicator of amplification may be presented by each of the plurality of sample reaction volumes that host amplification of a nucleic acid molecule (e.g., amplification of the target nucleic acid molecule).

In an embodiment, one or more dyes may be used that fluoresce when bound to double-stranded nucleic acids, and this fluorescence may be detected as an indicator of amplification. For example, the nucleic acid binding agent (dye) may produce a detectable signal when bound to double-stranded nucleic acids that is distinguishable from the signal produced when that same agent is in solution or bound to a single-stranded nucleic acid. The fluorescence may be detected using a fluorescence detector, for example mounted over a chip that houses the segregated sample reaction volumes, or may be detected in any other suitable manner. Further, sample reaction volumes may be housed on a plurality of devices, such as a plurality of chips, where each chip may generate data based on the indicators of amplification detected from the respective sample reaction volumes. In various embodiments, the generated data may be visualized, for instance using a graphical user interface (GUI).

In various embodiments, optical systems may be used in combination with chip 200. For example, an optical system may have an illumination source that emits electromagnetic energy, an optical sensor, detector, or imager for receiving electromagnetic energy from reaction volumes, and optics used to guide the electromagnetic energy from reaction volumes to the sensor/imager/detector. For example, the sensor/imager/detector may be configured to detect fluorescence exhibited by the sample reaction volumes and generate data, as described herein, based on the sensed fluorescence. In some embodiment, the optical system may comprise a QuantStudio™ 3D instrument, or any other suitable system or device.

As an alternative to low reaction volume chambers as described above for carrying out nucleic acid amplification monitoring in a stationary sample, the sample may be caused to flow through a channel or chamber of a microfluidic device and as it flows it may be subjected consecutively to different temperatures whereby thermo-cycling is achieved. Thus, for example, the sample may be caused to flow through a channel or chamber which passes consecutively through different temperature zones suitable for the amplification stages of denaturing, primer annealing and primer extension, e.g. a channel in a microfluidic device, such as, for example, a silicon chip device, which passes consecutively through zones of different temperature provided in the base suitable for successive repeats along the channel of the stages of denaturing, primer annealing and primer extension. Such microfluidic structures for performing continuous flow nucleic acid amplification on a chip are described, for example, in Auroux et al., Minaturised Nucleic Acid Analysis Lab Chip (2004) 4, 534-546. Structures of this type may be fabricated through the use of standard microfabrication techniques using for example photolithography to define the fluidic network and then an etching or deposition step to create the required channel or channels, for example in a PMMA, acrylic, Perspex™ or glass substrate. A cover plate in glass or PMMA or other material may or may not be overlaid to cover the channels. The base of the channel or channels may be formed by substrate bonding to a silicon chip and temperature sensors as well as heating or heat pump (Peltier) elements, such that the reaction mixture is in direct contact with these sensors and actuators, and may or may not include circuitry for temperature control.

Alternatively, the base of the channel(s) may be formed by a printed circuit board (PCB) housing temperature sensors such that these are in direct contact with the reaction mixture. The PCB may also house heating or heat pump elements, sensor interface and temperature control circuitry. Reagents present within the microfluidic channel or chamber may be those of the buffered amplification reaction mixture, which may include the primers chosen for ability to hybridize to the target at sites suitable for amplification of the chosen sequence, the required enzyme or enzymes for amplification and all four dNTPs in excess.

Temperature control may be achieved by a proportional-integral-derivative (PID) controller, which is one of the most common closed-loop feedback control systems. Errors between the measured temperature and the target temperature may be then used to calculate the level of heating required. Calculation of this output level may be performed based on the current error directly (proportional), the history of the error (integral), and the predicted future error based on its rate of change (derivative). Similarly, a PI controller may stabilize temperature based on present and historical values of the error as described in Iordanov et al. (2004) ibid. Alternatively, techniques such as pulse-width modulation or duty-cycling may be implemented.

It may alternatively be chosen to have a reciprocating system whereby the amplification mixture is moved backwards and forwards in a microchamber between the required temperature zones for thermo-cycling. As an alternative to contact heating for thermo-cycling, various noncontact heating methods may be employed as also discussed in the same review article, including by way of example hot-air mediated heating, utilization of IR light, laser-mediated heating, induction heating and microwave irradiation.

In various exemplary embodiments in accordance with the present disclosure, digital nucleic acid amplification (e.g., dPCR) may be performed using a microfabricated chip that includes an array of reaction chambers into which the sample is segregated into separate reaction volumes (sample portions) upon being introduced to the device. In such a device, the sample portions remain in their individual reaction chambers while subjected to the amplification assay, including for example the various stages of thermal cycling.

In other embodiments, reaction volumes may be segregated using droplets. For example, a plurality of droplets may be generated using a device, for instance, by drawing a sample and oil through a nozzle. The droplets may be approximately 1 nL in an embodiment. The droplets may then be transferred for thermal cycling such that PCR amplification may be achieved. For example, the droplets may be transferred to a PCR plate or a chip with reaction chambers, and a thermal cycler may be used to cycle the droplets through phases of amplification. The droplets may then be exposed to a reader in order to determine amplification results. For instance, the PCR plate or chip may be loaded onto a reader that draws the droplets from each reaction chamber and exposes them to a reader (such as a detector that measures fluorescence). In some examples, the droplets may be droplets in a free solution.

In another embodiment, after generation of the droplets, a flow based technique may be used to perform thermal cycling. For example, the droplets may be caused to flow through a channel or chamber which passes consecutively through different temperature zones suitable for the amplification stages of denaturing, primer annealing and primer extension, e.g. a channel in a microfluidic device, such as, for example, a silicon chip device, which passes consecutively through zones of different temperature provided in the base suitable for successive repeats along the channel of the stages of denaturing, primer annealing and primer extension. Similarly, the droplets may then be exposed to a reader in order to determine amplification results.

In some embodiments, reaction s sites may be used to segregate a sample and such that an amplification assay may be performed. The reaction sites may comprise through-holes, wells, microwells, droplets, or any other suitable reaction site that may host a sample for exposure to an amplification assay.

According to various embodiments described herein, to help a user identify data for further analysis based on quality, for example, different data visualizations may be generated by a processor for displaying to a user. For example, a GUID may allow a user to select a chip or reaction device whose data the user wishes to view. Based on the PCR (e.g., qPCR or dPCR) and detection techniques described herein, data may be generated for one or more chips or reaction devices that have performed the techniques described herein. The generated data may be grouped according to respective chip or reaction device and displayed in a menu for a user to select. When a user selects a chip or reaction device to view, the corresponding data generated by the selected chip or reaction device may be displayed in various ways so that a user may identify the positive reactions in the plurality of reactions sites. For example, where fluorescence detection is used to generate the data, the graphical depiction of the data may represent the fluorescence detected for particular reaction sites on the chip after performing amplification (e.g., dPCR amplification).

Further, a user viewing representations of the positive reactions and positions of positive reactions may be able to better identify any errors or aberrations in the data or in the experiment. For example, insufficient loading of the sample into a plurality of reaction sites in one portion of a chip may be obvious from a data visualization of the chip. Because of the large number of reaction sites in a chip, to be able to usefully view the positive and negative reactions, the chip may visualized in a plurality of portion views. In this way, the user may be able to view a display of positive reaction in smaller portions. For example, a first quadrant of data 306 may be selected by the user to view. In other examples, the data from three other quadrants of the chip 210 may be available to view when the user selects them.

Data visualizations in known user interfaces often provided chip data in the form of heat maps that show the positive or negative classification status of each individual reaction site (for example, through-holes), or optionally, the quality value for each through-hole. In various embodiments, heat map refers to the intensity of fluorescence detected across a given chip. Conventionally, this data was often provided in a heat map interface, or tab, separate and non-integrated from another separate tab where the chip data, provided in a cluster plot (or scatter plot) view, was available for manual calling functionality. This separation and non-integration impacted a user's ability to efficiently determine if rare points on the cluster plot were located on stable regions of the chip (e.g., regions that do not appear to suffer from faulty loading, or some other error).

Figure 3:
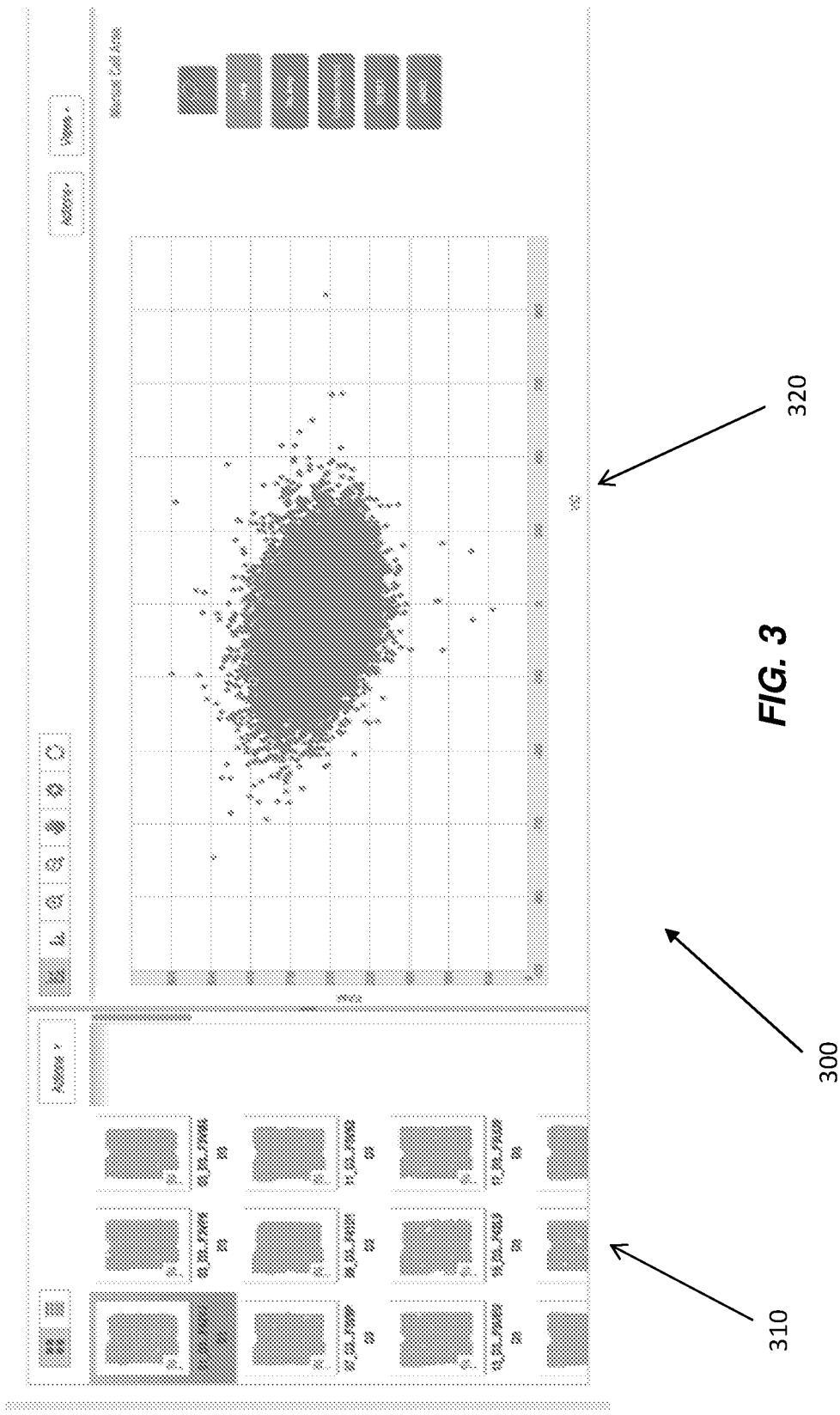
FIG. 3 illustrates a data visualization with generated chip thumbnails and generated cluster plot according to various embodiments.

In an embodiment of the present disclosure, FIG. 3 illustrates data visualization 300, which can be provided on a graphic user interface (GUI), which advantageously provides a single view where chip thumbnails 310 are co-located with corresponding cluster plot 320.

Figure 4:
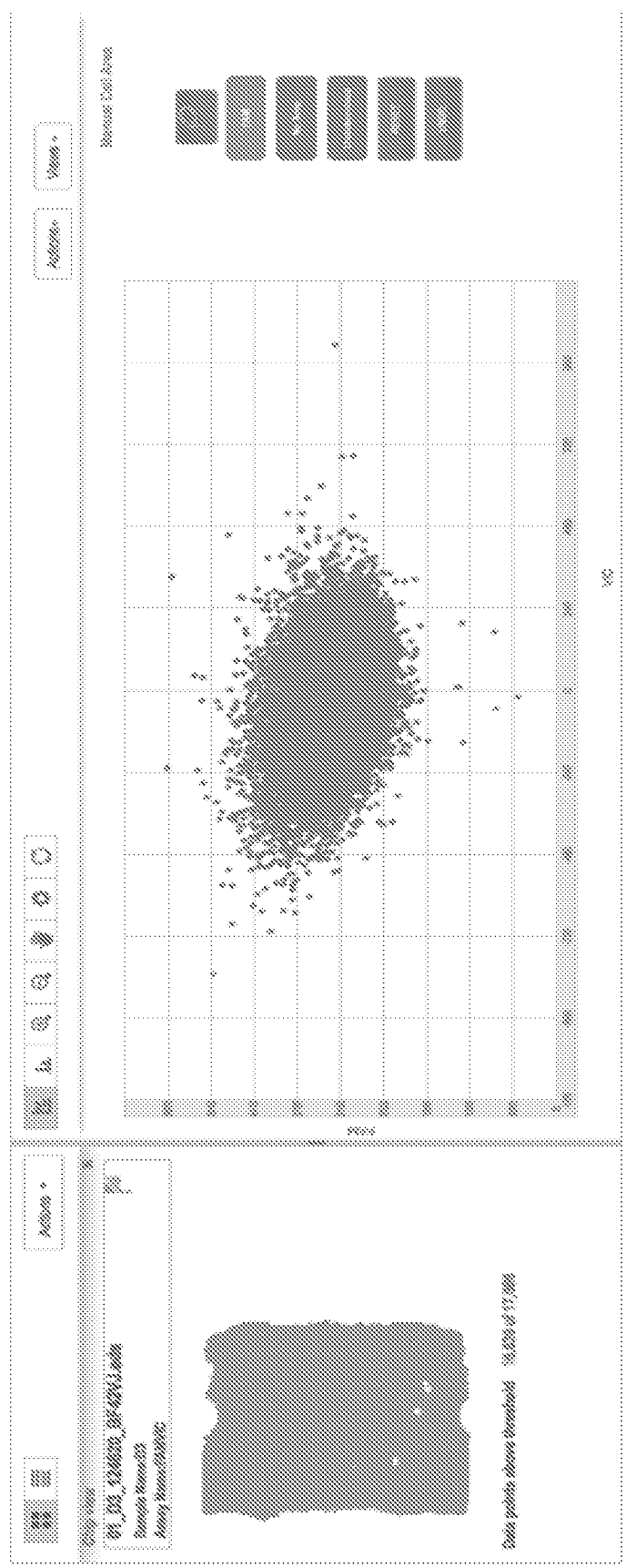
FIG. 4 illustrates a data visualization with a generated chip heat map and generated cluster plot according to various embodiments.

By co-locating (for example, side by side as illustrated in FIG. 3.) chip thumbnails 310 with cluster plot 320, a user can select specific thumbnails to expand the chip to a heat map view 410 for that specific chip, as illustrated in FIG. 4.

Further, a user may select specific data points or groups of data points (which correspond to reaction sites and/or reaction volumes) and individual identify, or call, whether the data points indicate presence of a target nucleic acid (e.g., whether the corresponding reaction volumes hosted amplification of the target nucleic acid). For instance, in an embodiment where two nucleic acids are targeted (e.g., a wild-type and a rare) using two individual probes (e.g., FAM™ and VIC®) the potential calls comprise no amplification, amplification of a first of the target nucleic acids, amplification of a second of the target nucleic acids, and amplification of both target nucleic acids. In some embodiments, an algorithm may be used to identify, or call, the generated data points, as further described below. However, some data points may be identified as unknown, for instance if the algorithm is not able to make a call with a minimum degree of confidence, or the algorithm may call some data points incorrectly. Accordingly, a user may manually make calls to enhance the accuracy of the calls, and ultimately the accuracy of the quantification of amplified target nucleic acids. In some embodiments, called data points (e.g., automated or manually) may be identified by predetermined colors (not illustrated).

In some embodiments, when a user makes individual calls on the cluster plot, the system processor will process such user input to output, via the GUI co-location feature, a data visualization that immediately reflects those calls on the corresponding heat map for the selected chip. In some examples, the immediate reflection may comprise displaying the calls using a predetermined color.

The edge of the chip can be subject to effects such as, for example, evaporation and optical distortion, much more so than the center of the chip. These effects may cause a through-hole without actual template to glow more brightly (e.g., increased fluorescence) than the main negative population (e.g., data points identified, or called, as corresponding to reactions volumes without amplified target nucleic acids). In this case, the fluorescence level is indicative of an artifact of the system rather than an actual amplification.

Figure 5:
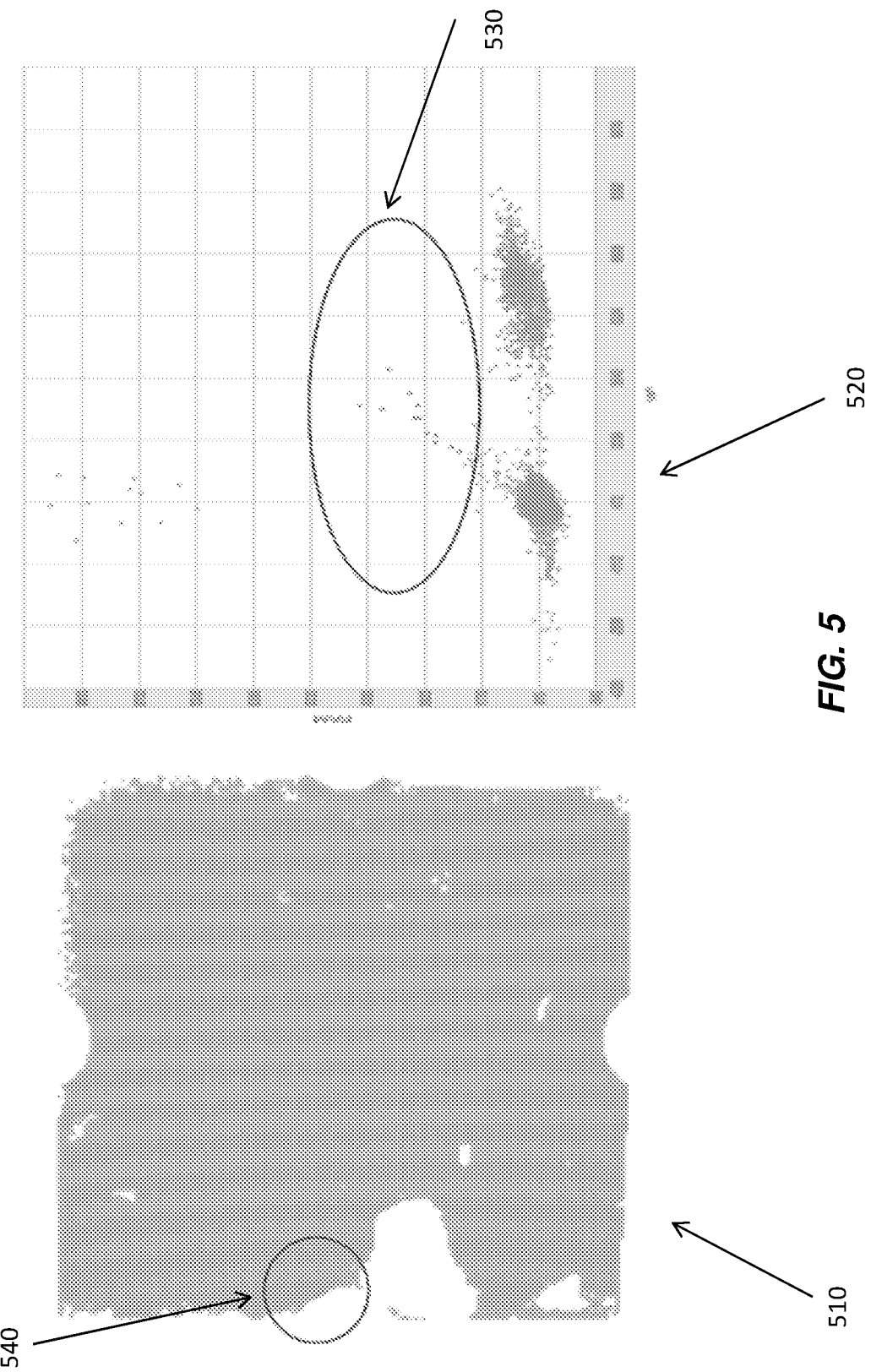
FIG. 5 illustrates a data visualization with a generated chip heat map and generated cluster plot according to various embodiments.

In applying the co-location feature, a user can identify a data point(s), for example, at the edge of a cluster on the cluster plot, which may be an artifact. The user can then isolate that data point, or points, and identify the point(s) as undetermined rather that either positive or negative. For example, the user may use a lasso, as illustrated in FIG. 5, to identify, or call, the data points as undetermined. A lasso may comprise a pointer that can be manipulated by the user to create a free form shape such that that data points within the shape may be manually identified or called. In some embodiments, rather than a pointer, a touch interface may be implemented to manually call out data points. Any other suitable interface such that data points may be selected on a display may similarly be implemented. The system processor processes the user input and outputs instructions to the co-location feature to immediately visualize the lassoed data point, or points, in the corresponding chip heat map. If, for example, a group of these potential artifacts are not uniformly distributed or appear to be edge artifacts, a user can then directly ascertain if those data points can be labeled as undetermined, and in some embodiments, these points may then be excluded from analysis.

Figure 6:
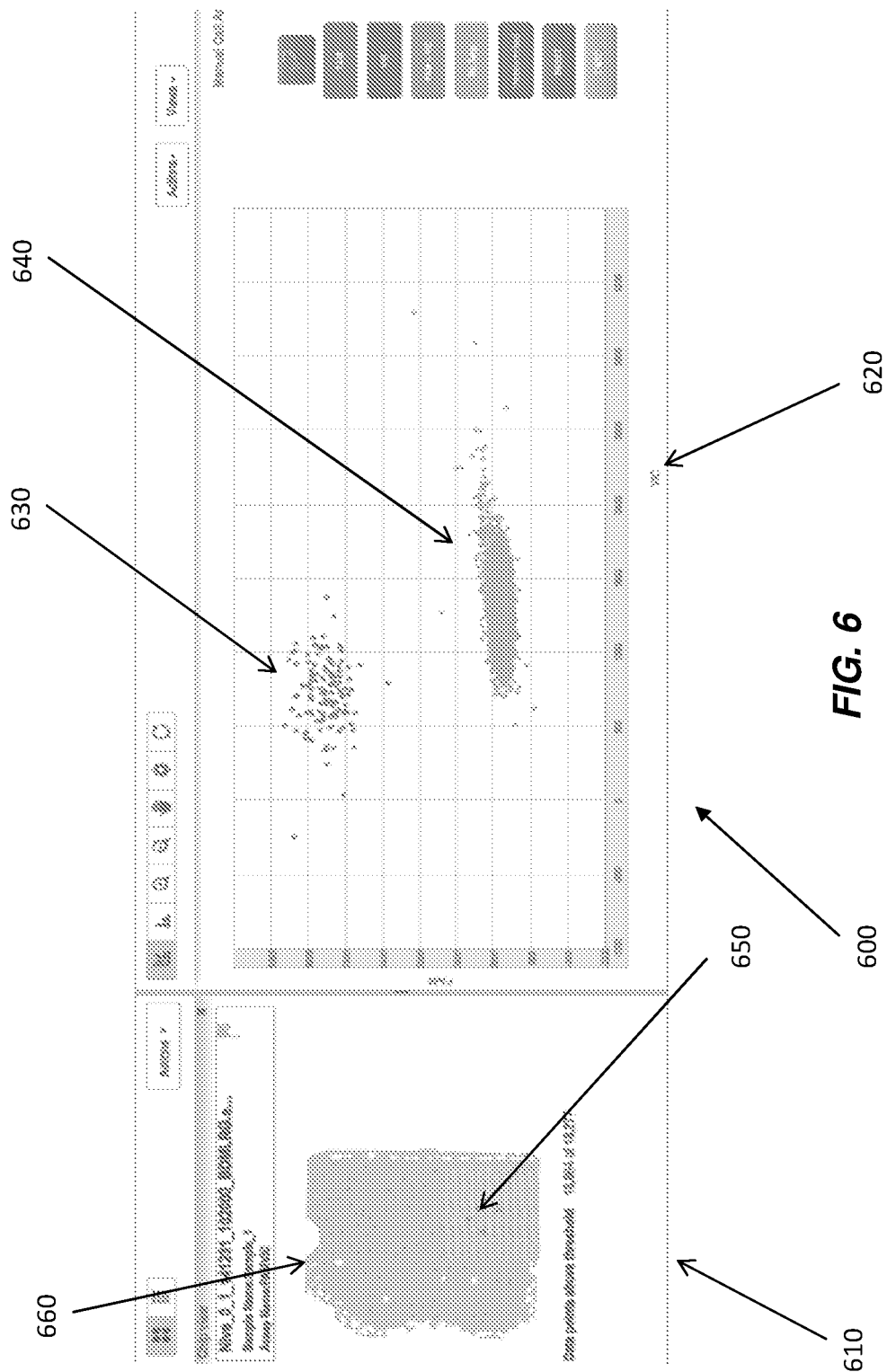
FIG. 6 illustrates a data visualization with a generated chip heat map and generated cluster plot according to various embodiments.

In another embodiment of the co-location feature, a user identifies a data point (or multiple data points) that form(s) a rare point or cluster. Referring again to FIG. 5, a user employs a capture (or isolation) tool (e.g., lasso) to capture (or encircle) the rare cluster 530 on the cluster plot 520, review the corresponding captured rare cluster 540 on the heat map 510 (circles on FIG. 5 added for emphasis), and immediately determine if this rare cluster is located in a region of high data quality, and not placed around areas at increased risk of erroneous detection. FIG. 6 provides another illustration of this feature, as a data visualization 600 in practice may show a different color (not illustrated) to the captured cluster 630 versus the remainder of the data points 640 on cluster plot 620. The co-location feature provides a corresponding alteration to heat map 610 (not illustrated), differentiating the captured chip points 650 from the remainder of the chip points 660 (e.g., in some embodiments, with a different color).

Figure 7:
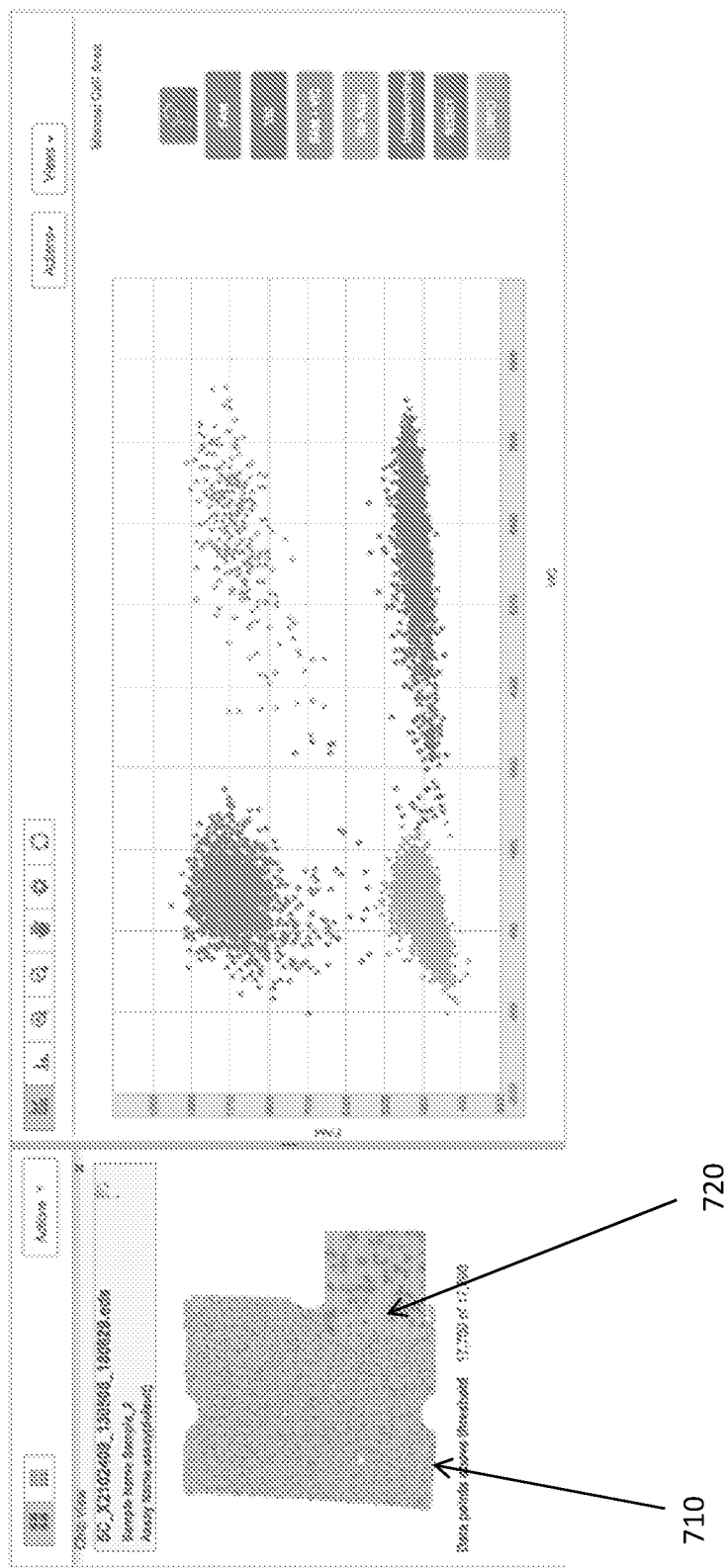
FIG. 7 illustrates a data visualization with a generated chip heat map and generated cluster plot according to various embodiments.

Referring to FIG. 7, in an embodiment the co-location feature of the GUI can also allow the user to zoom over portions of the heat map 710 to see data points more closely, thus additionally helping the user to verify that data is coming from a stable region of the chip. The zoom feature can be present, for example, in the form of a magnifying glass 720, which can be employed, for example, by moving the tip of a mouse cursor over heat map 710 with magnifying glass 720.

In known data visualizations for dPCR applications, if users desire to overlay multiple chips onto a single scatter-plot for comparison, users were often required to search for the relevant chips. For example, during practical application, users will often run positive controls and negative controls and, thus, will want to call unknown samples based upon signal levels of the control chips. Searching for relevant chips in this example, or generally for that matter, can prove cumbersome given the capabilities of dPCR applications to store data for numerous chips as well as the user need to perform dPCR on numerous relevant and related chips at one time. As a result, it would be advantageous for the GUI system processor to identify and separate a relevant group of chips based on user selection of given grouping options.

Figures 8A, 8B:
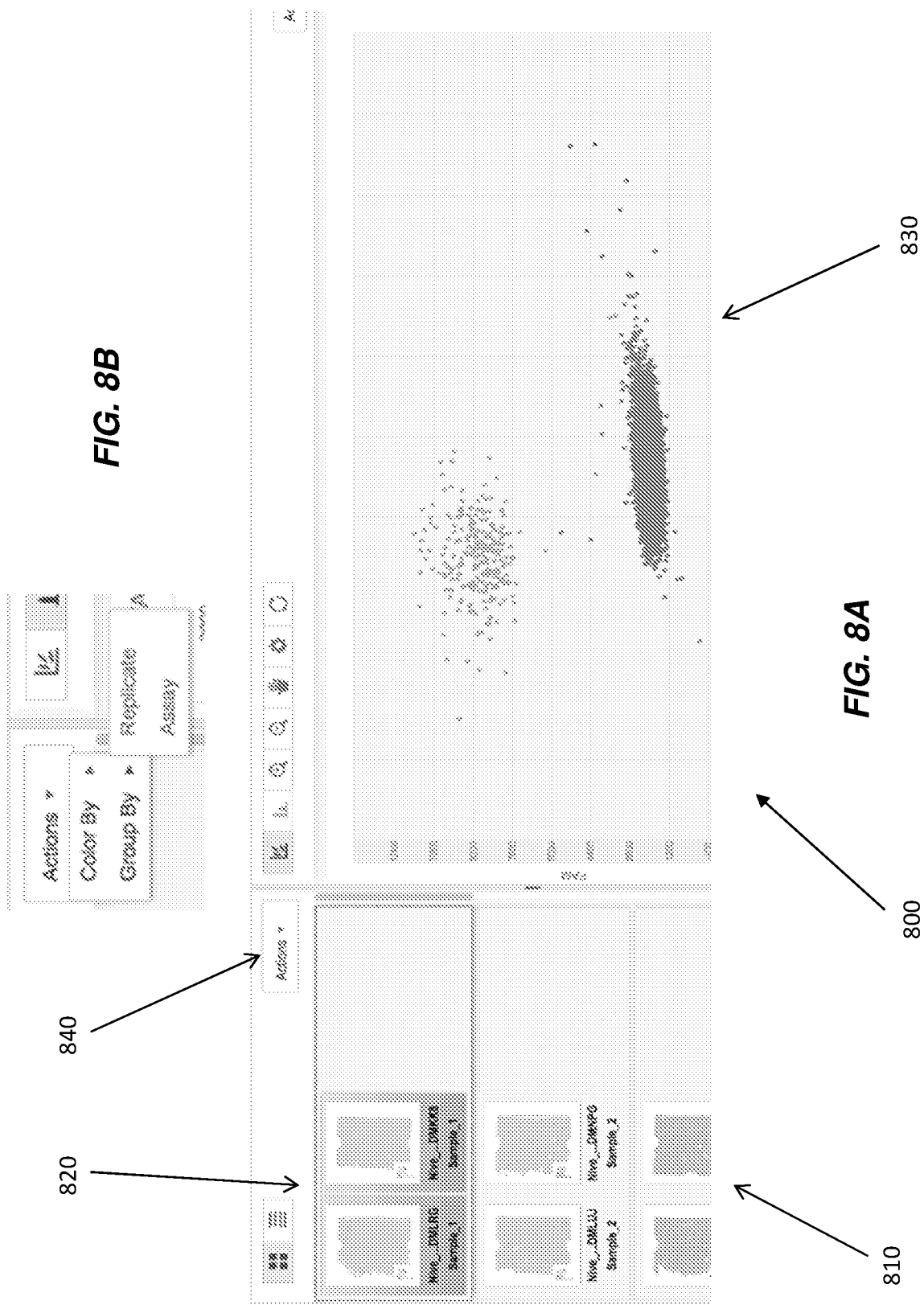
FIGS. 8A-B illustrate a data visualization with generated chip thumbnails and generated cluster plot according to various embodiments.

In another embodiment of the disclosure, illustrated in FIG. 8A, data visualization 800 is provided that outputs a re-ordering of chip thumbnails 810 into a chip grouping 820, according to chosen filtering or grouping options provided to the user. Grouping 820 can then be overlaid onto co-located scatter-plot 830. Grouping or filtering options can include, but are not limited to, grouping or filtering by replicate or assay type, where replicate can include chips with the same assay and sample names, yet that may also cover a range of dilutions. In visualization 800, a user can select the option via a data manipulation tool 840, which can be, for example, a drop-down menu, tab selection, or box selection. A drop-down menu is illustrated in FIG. 8B in expanded form as one example of tool 840.

In digital PCR, two common data analyses are absolute quantification (AQ) and relative quantification (RQ). In absolute quantification using digital PCR, the target of interest is directly quantified with precision determined by the number of digital PCR replicates. For example, if a user seeks to quantify copies of a rare allele present in heterogeneous mixtures, the AQ application counts the number of cell equivalents in the sample by targeting genomic DNA, and then determines the absolute number of viral copies (e.g., based on detected fluorescence levels associated with a target nucleic acid corresponding to the rare allele) present in a given sample without reference to a standard. By contrast, the RQ application analyzes changes in gene expression in a given sample relative to another reference sample (such as an untreated control sample). For example, if a user seeks to measure the gene expression in response to a drug, the RQ application would compare the level of gene expression of a particular gene of interest in a chemically-treated sample relative to the level of gene expression in an untreated sample.

Conventionally, AQ and RQ applications, and thus the corresponding data visualizations, are provided as separate, non-integrated (or synchronized), applications as users commonly use the two applications independently. Specifically, AQ applications generally provide a display of a histogram such as, for example, the histogram 910 illustrated in FIG. 9. However, conventionally, (a) the histogram itself is not co-located with an associated cluster plot and (b) the data represented on the histogram is not synchronized with the data presented by a cluster plot. Similarly, RQ applications generally provide a display of a cluster plot such as, for example, the cluster plot 920 illustrated in FIG. 9. However, conventionally, (a) the cluster plot itself is not co-located with an associated histogram and (b) the data represented on the cluster plot is not synchronized with the data presented by a histogram.

Figure 9:
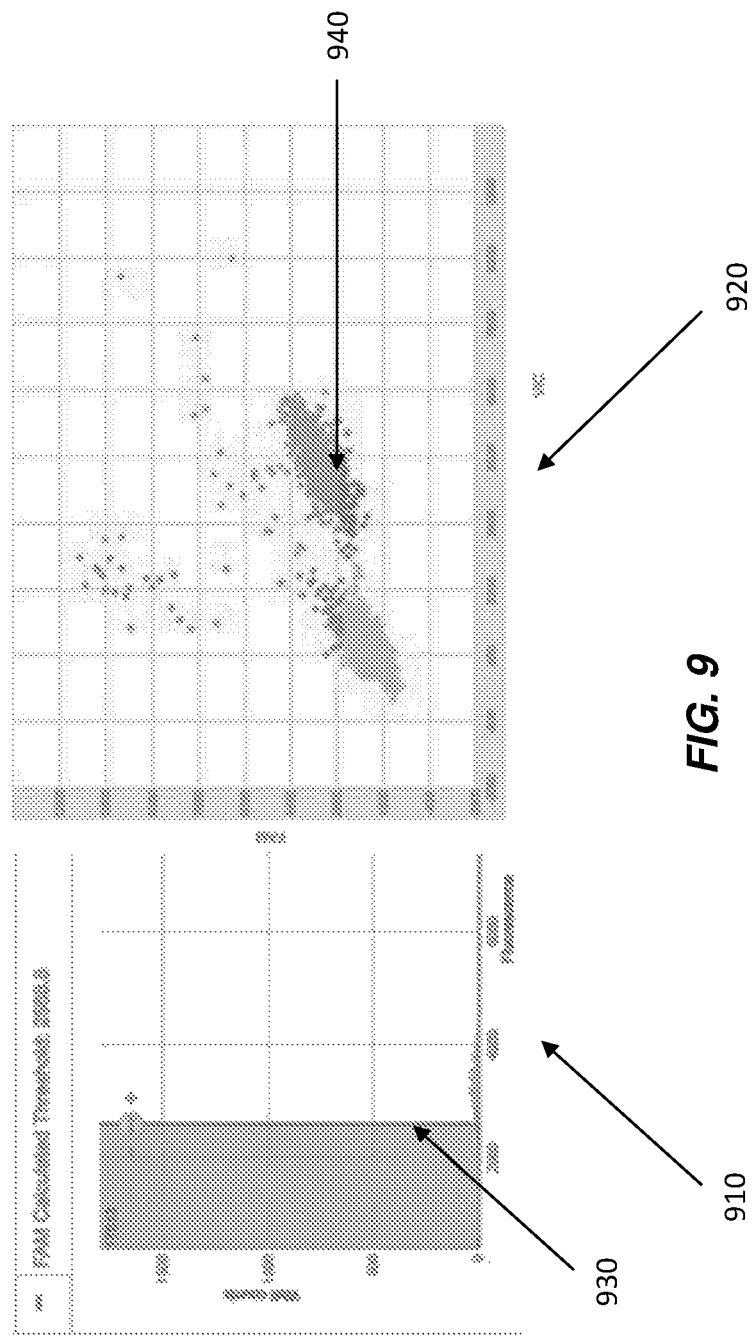
FIG. 9 illustrates a histogram of fluorescent values and a cluster plot from a plurality of data points according to various embodiments.
Figure 10:
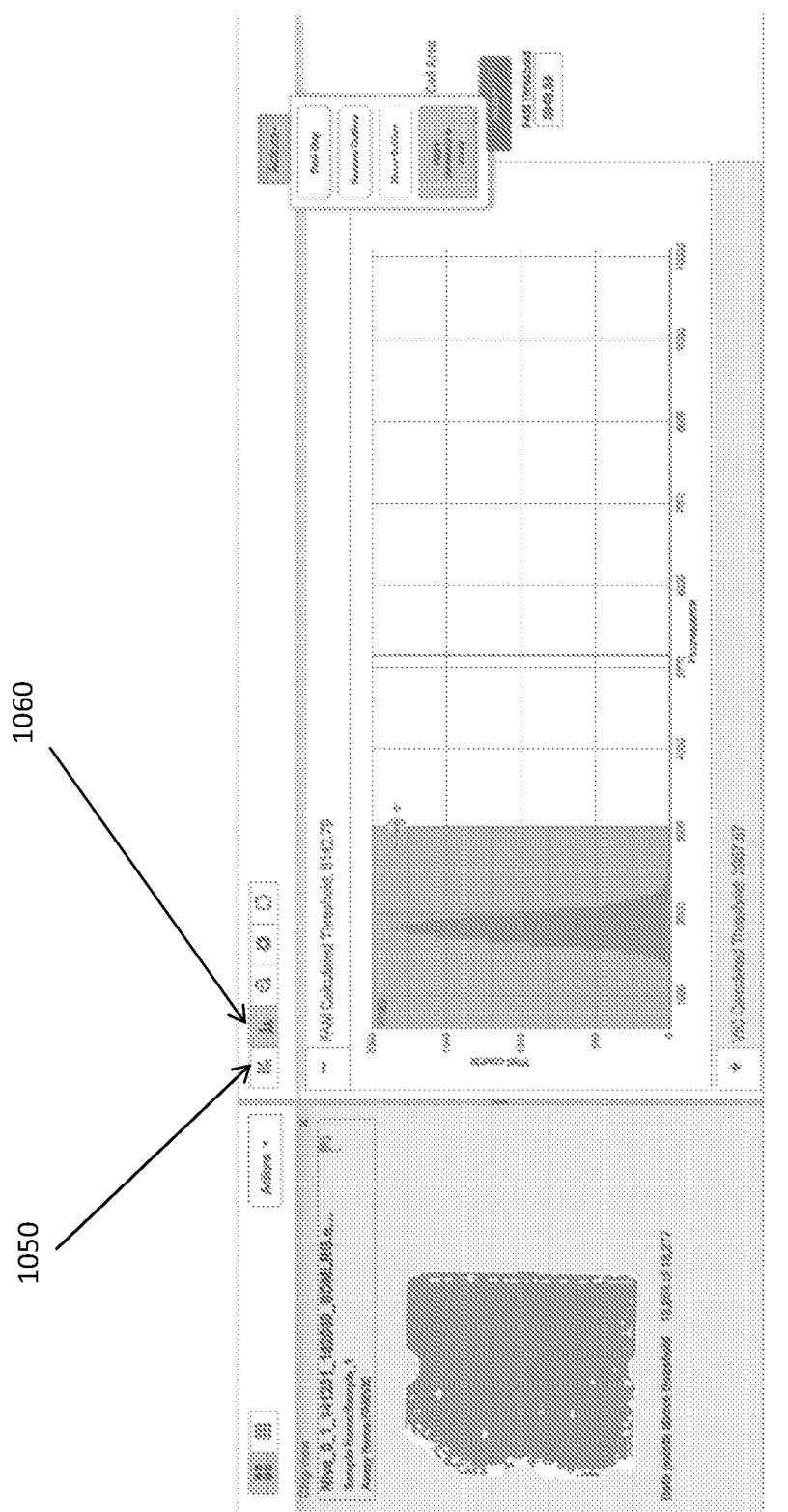
FIG. 10 illustrates a data visualization with a generated chip heat map and generated histogram according to various embodiments.

It would be advantageous integrate the visualizations of a cluster plot with a histogram so that the same data is available in both views, allowing real-time updating of the cluster plot and vice versa. In an embodiment of the disclosure, illustrated in FIG. 9, histogram 910 and cluster plot 920 are co-located, making real-time updating viewable concurrently. However, even if the histogram and cluster plot are provided on two different tabs, having the views integrated with the same data increase the accuracy of a user call on a single data point, multiple data points, or a cluster of points, particularly because the user will now have the capability to make calls in either visualization, but have both visualizations available to make a more informed decision. FIG. 10 illustrates a cluster plot integrated with a histogram, where the cluster plot is viewable from first tab 1050 and the histogram is viewable from second tab 1060 (histogram shown on FIG. 10). Even though provided on two different tabs in this example, the visualization outputs are easily compared by clicking adjacent tabs 1050 and 1060 as desired.

For example, some data sets provide clusters that are not as horizontal or as vertical as preferred. Non-specific amplification in a second dye may cause the clusters to look somewhat diagonal. The problem, in this situation, is a histogram of the other dye will give the appearance of two distinct humps, which may cause the user to determine a threshold at an incorrect fluorescence level, not where the true separation is located. Histogram 910 of FIG. 9 illustrates the incorrect fluorescence level 930. In some embodiment, this error can be viewed when analyzing that threshold on cluster plot 920 at fluorescence level 940. Having the ability to view the same data in both visualizations helps to prevent these types of misinterpretations.

On the other hand, even with data sets that are not as misleading, the synchronization of views is also advantageous. For example, as illustrated in FIG. 10, if the data shows an expected horizontal (or vertical) pattern, integrated visualizations between, for example, the chip thumbnails, cluster plot and histogram, provide the user the ability to call using thresholds in the histogram and propagate the thresholds to all chips with the same assay assigned on it. This provides an objective way to propagate call settings rather than use of manual capture tools such as the lasso of FIG. 5, which are not as repeatable as an automatic propagation across multiple chips.

Figure 11A:
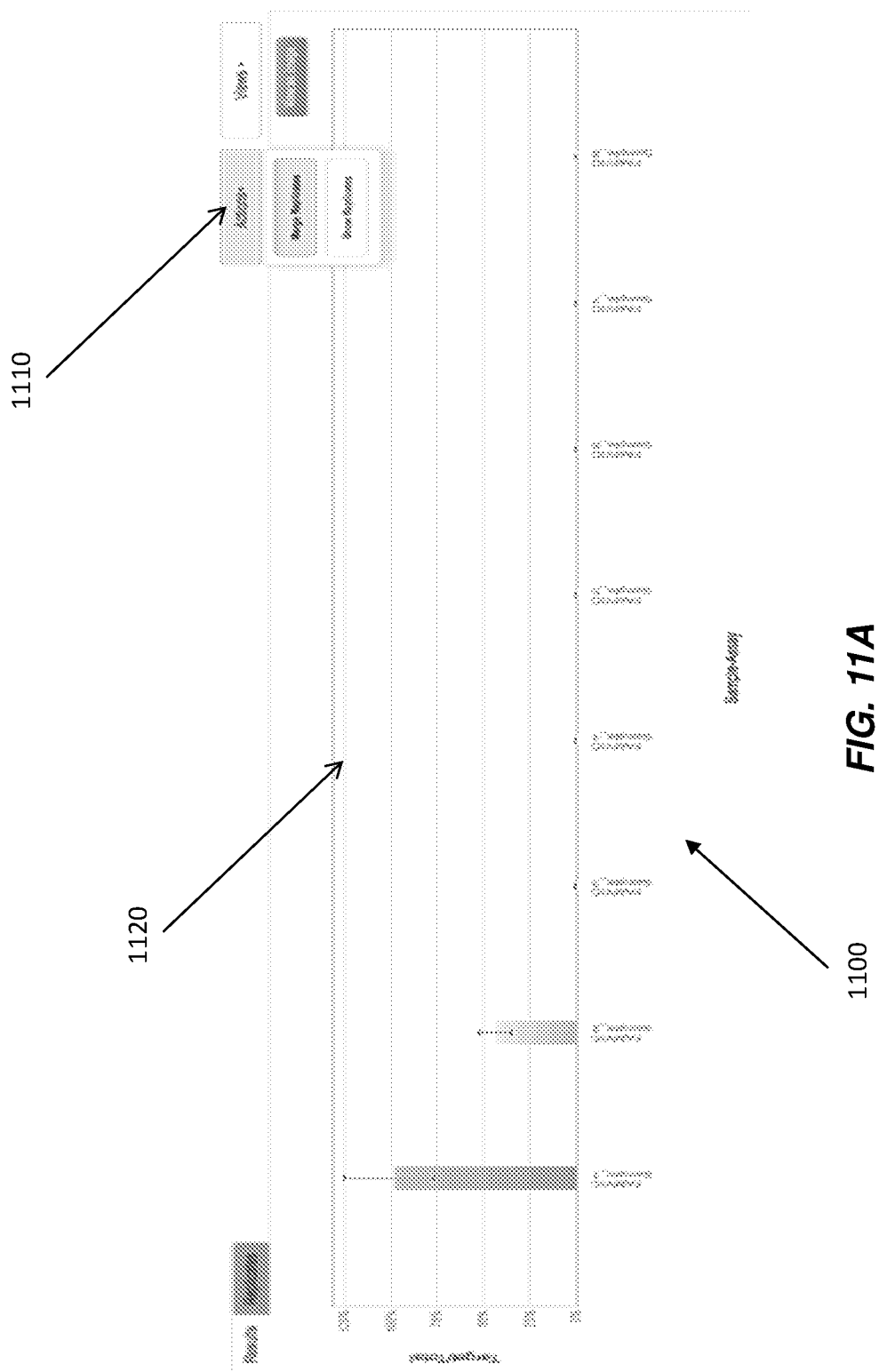
FIGS. 11A-B illustrate a data visualization with a generated bar chart according to various embodiments.

Generally along with data manipulation and comparison features, examples of which were described above, users will desire to see final quantification results. Conventionally, these results have often been provided only at the assay-sample quantification level. casein some embodiments, replicate chips were all treated as one virtual chip, therefore not accounting for chip to chip variation. FIG. 11A illustrates an assay-sample quantification level bar chart. It would be advantageous to be able to provide a user with multiple views of quantification results to include, not only the assay-sample quantification level views (which are beneficial), but more granular views, to provide more information to the user.

In an embodiment of the disclosure, a data visualization is provided that includes multiples views of differing granularity. These views can include, but are not limited to, a view with replicates merged, and a view with replicates shown. Again, as illustrated in FIG. 11A, a data visualization 1100 is provided that includes a results manipulation tool 1110, which can be, for example, a drop-down menu, tab selection, or box selection. A drop-down menu is illustrated in FIG. 11A in expanded form as one example of tool 1110. As illustrated, the "merged replicates" is selected, thus resulting in the output of an assay-sample quantification level bar chart 1120.

Figure 11B:
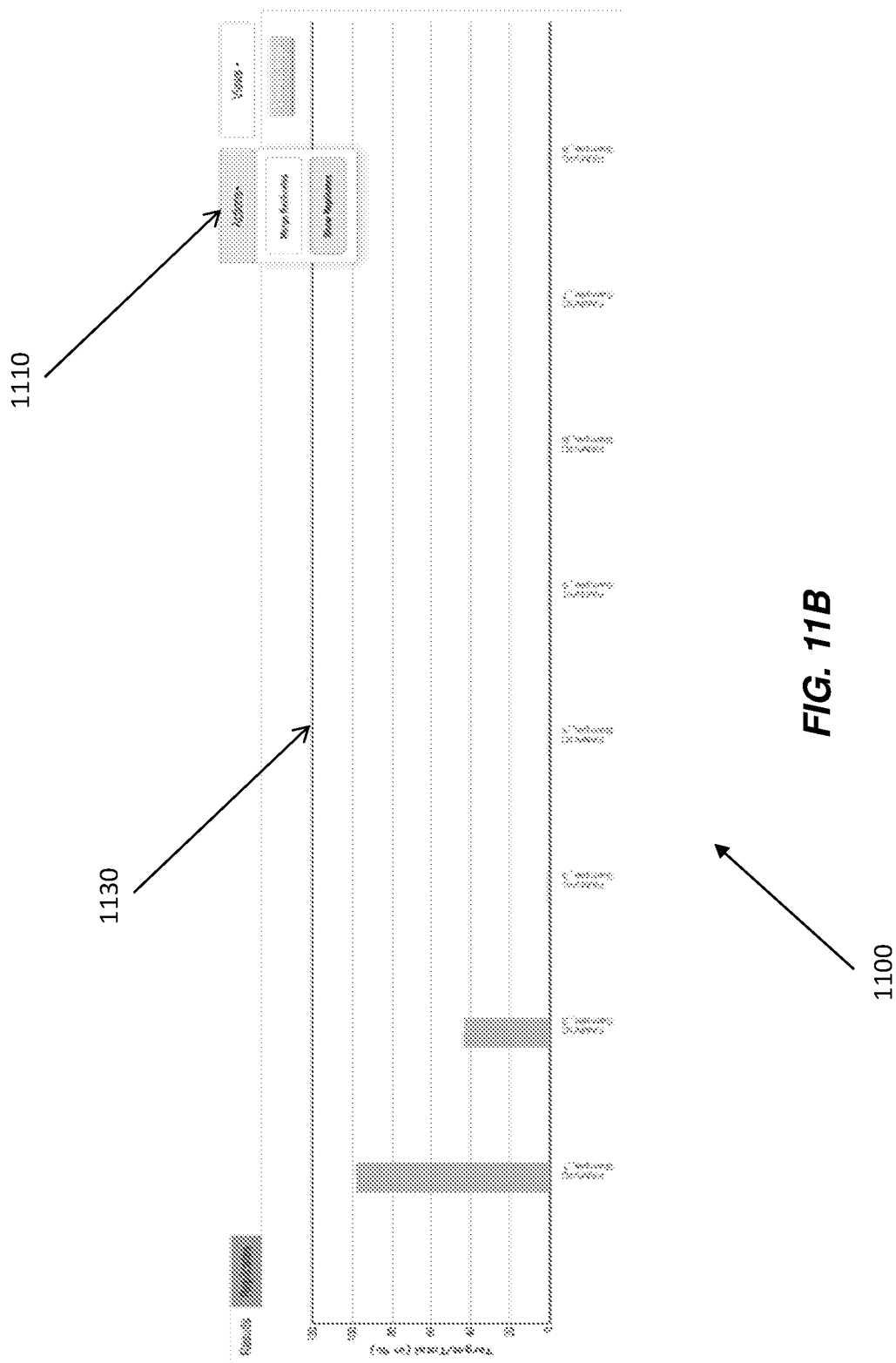

FIG. 11B, on the other hand, illustrates selection of "show replicates" from tool 1110. Upon selection of this option, the system processor weighs the data from different chips to account for chip to chip variation and outputs instructions to graphically display a replicate level bar chart 1130 as FIG. 11B. Bar chart 1130, besides revealing replicates, can also provide the merged replicate bars of FIG. 11A. The merged replicated bars can be set back from the replicate bars such that the replicate bars are overlaid onto the merged replicate bars. This can be accomplished, for example, by setting back the merged replicate bars in grey. Providing visualizations that compare the combined result to the result from individual replicates advantageously provides more results information to user.

While some of the data visualization embodiments described above reference a particular reaction device, such as a chip, any suitable reaction device capable of performing PCR amplification may be implemented. For example, as an alternative to carrying out nucleic acid amplification monitoring in a stationary sample, the sample may be caused to flow through a channel or chamber of a microfluidic device and as it flows it may be subjected consecutively to different temperatures whereby thermo-cycling is achieved. Further, as an alternative to reaction chambers, through-holes, or microwells, droplets may be formed and used to perform low volume PCR amplification. The data visualization techniques described herein, as well as the data analysis techniques, may be applied to PCR results obtained from any suitable reaction device or system.

In some embodiments, the graphical user interface may be used to adjust a criteria or threshold that configures the automatic calling of data points. For example, various algorithms are disclosed and compared herein, and advantages related to the disclosed embodiments are described.

In some embodiments, the algorithms and techniques described herein may be useful in identifying and otherwise quantifying rare targets. In a dPCR configuration, amplification is detected in sample reaction volumes with a nucleic acid template and no amplification is detected in sample reaction volumes lacking then nucleic acid template. For example, some embodiments may involve detection and quantification of rare alleles versus wild-type alleles. The large scale partitioning of dPCR isolates rare targets within a subset of partitions, elevates the rare to wild-type target ratio within any specific partition (compared to the original PCR mix), and enhances the amplification probability and detectability of the rare target. These effects enable detection of the rare target with high sensitivity.

Challenges associated with digital PCR experiments for rare allele detection include understanding the limit of detection of the assay and platform. Data points corresponding to rare target are by definition far fewer than the data points corresponding to positives for the wild-type target. This makes identification of the rare target challenging. One known approach to addressing this challenge requires overlaying wild-type control data with positive control data to guide the definition for a boundary of the wild-type event in fluorescence space. The data points outside of this boundary are considered true positives for the rare target for unknown sample (and false positives for a control sample with wild-type only target). A known method (method A) for solving this challenge is described below.

Known Method A

The data from the wild-type control is overlaid with the data from the positive control to guide the definition for a boundary of the wild-type event in fluorescence space. The data points outside of this boundary are considered true positives for the rare target for unknown sample (and false positives for a control sample with wild-type only target). This technique works when the inter-run variation in signal levels is negligible or when a specific normalization is applied to account for such variation, but may run into challenges when these are not a given.

A more reliable method (Method B), according to various embodiments, for solving this challenge is described below:

Method B

A second approach, described in the present disclosure, identifies the center of the non-amplification cluster and of the wild-type positive cluster. This approach next evaluates, for each data point, the probabilities {p1,p2} of belonging to either of these clusters. The final step establishes, again for each data point, a single probability, p=max{p1, p2}), upon which a threshold may be applied to identify outlier events that do not belong within one of these main clusters. This strategy is more robust as it works independent of inter-run variations in signal levels. It is based on the assumption of finding a sizable non-amplification and wildtype positive clusters. In experiments that involve rare allele detection, such clusters can be expected.

If false positives are identified using control chips, lower limits on detectable concentration of the rare target can also be established. Replicate runs may be used to get an understanding of the distribution of false positive events for a given assay system. Then, a lower limit of detection (above the false positive rate) of the assay system can be calculated, as further described below.

The present disclosure relates, in some embodiments, to a method for identifying false positive events in the detection of rare targets. The method can include identifying the center of the non-amplification cluster and of the wild-type positive cluster. This method can also include evaluating, for each data point, the probabilities (e.g., {p1,p2}) of belonging to either of the identified clusters. This method can further include establishing, for each data point, a single probability (e.g., p=max{p1,p2}) upon which a threshold may be applied to identify outlier events that do not belong within one of these main clusters.

This method is more robust than known approaches to false positive assessment strategies as it works independent of inter-run variations in signal levels. It is based, among other things, on an assumption of finding a non-amplification and wild-type positive clusters.

This description below compares a known false positive assessment method to a method of the present disclosure, using the signal levels of the no-amplification cluster and the wild-type cluster where available. Once the false positive call rate is established, this description below outlines a method to determine the limit of detection of the assay and platform, at a given level of confidence.

Figure 12A:
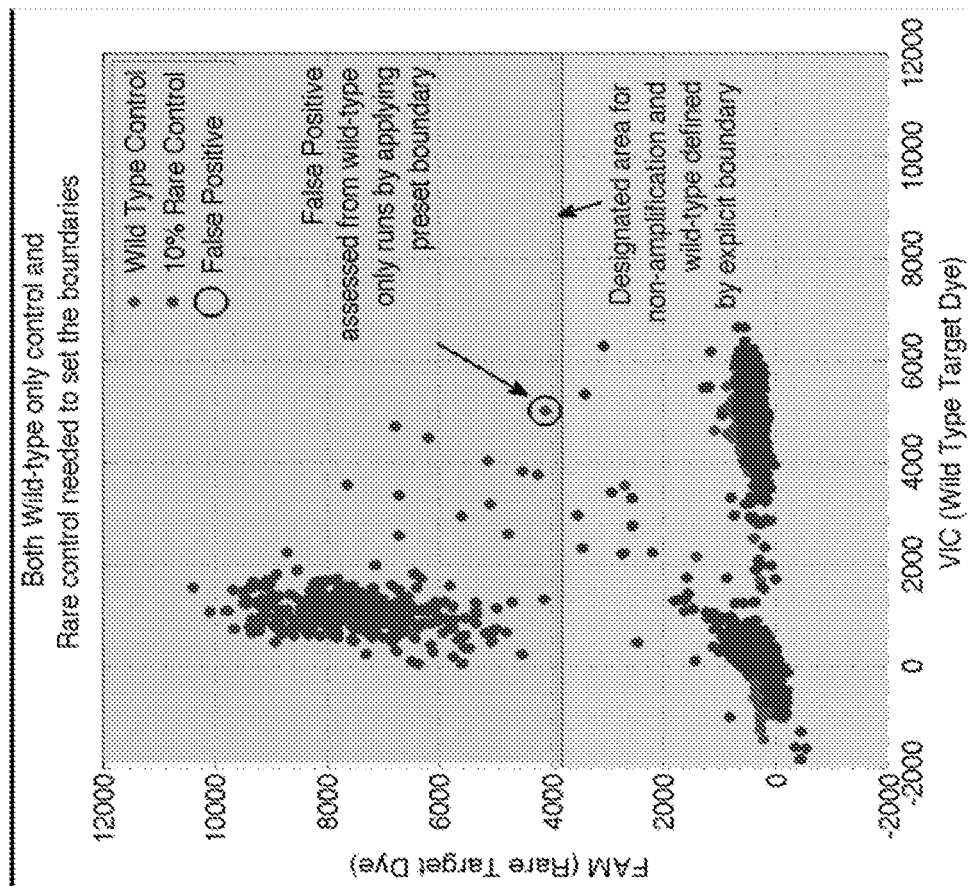
FIG. 12A and FIG. 12B shows two techniques for identifying false positives from non-template controls and wild-type control runs according to various embodiments.
Figure 12B:
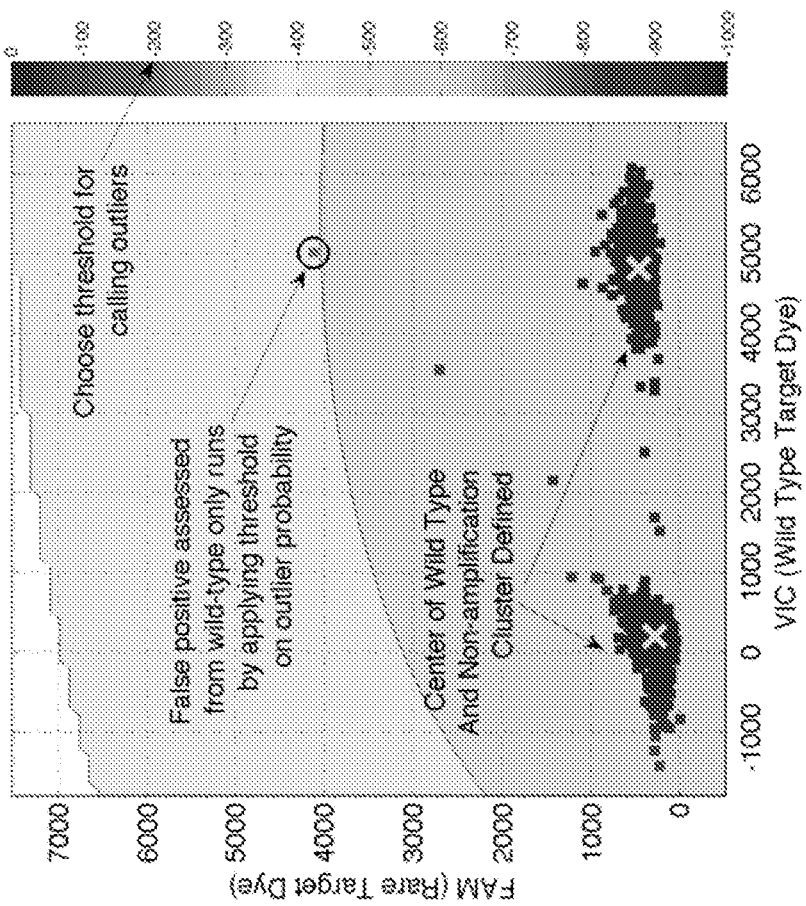

FIG. 12A and FIG. 12B shows two techniques for identifying false positives from non-template controls and wild-type control runs. FIG. 12A illustrates false positive identification based on a known method (Method A) of designating the non-amplification and wild-type positive cluster area in fluorescence space by explicit boundary, and designating points outside of this area designated as false positives. FIG. 12B illustrates a method in accordance with various embodiments disclosed herein for identifying false positives, the method including estimating cluster centers and spread respectively from the non-amplification and wild-type positives, fitting to a two dimensional Gaussian model (or any other suitable model), and applying a threshold on log probability for belonging to modeled cluster to identify false positives.

As discussed herein, it is a challenge to draw boundaries where the density of points is low, trying to decide whether or not a point on the edge of a cluster is a real positive or not, as necessary to apply Method A. Moreover, this method is susceptible to inter-run variation in signal levels. On the other hand, Method B can leverage identification of centers of clusters that have significant membership.

In some embodiments, the clusters may be identified based on histogram results for the amplification targets (e.g., wild-type and rare targets) and further based on the assays and target nucleic acids used for a given reaction. For instance, a given set of PCR reactions may use two dyes, one associated with a target wild-type and one associated with a target rare. In an example, a chip or reaction device may be configured as a wild-type control (where wild-type amplification is expected). With such a wild-type control, histogram data may be split into two groups, as a bimodal cluster associated with non-amplification data points and amplification of the wild-type data points is expected. The center of these clusters may be determined by identifying, for each cluster, the median values of the first and second dyes.

In another example, a chip or reaction device may be configured as a rare unknown or a rare positive control. In the rare unknown amplification of the wild-type and rare can be expected while in the rare positive control amplification of the rare can be expected. For these configurations, the histogram data may also be split into two groups, however the split may be performed in the dye space associated with the rare target. Then, for each group, using data points associated with the lower dyes values in each group (e.g., that comprise a first cluster of lower dye value data points), a median value of the first and second dyes may be identified as the centers of these clusters. Any other suitable technique to calculate these clusters given the data generated from the PCR amplification may be implemented.

Equation set 1 below describes the model used to calculate the likelihood of outlier status for a given data point, when both the non-amplification cluster and the wild-type positive cluster exists (wild-type control).

Let the probabilities p1 and p2 denote the probability of belonging with the non-amplification and the wild type positive cluster respectively.

$$p_1(v, f) = C \times \exp\left[-\frac{1}{2} A \sum_A^{-1} A^T\right]$$

$$p_2(v, f) = C \times \exp\left[-\frac{1}{2} B \sum_B^{-1} B^T\right]$$

where:
C is the constant associated with the 2D Gaussian modeling (Here, C=1)

$$A = \begin{pmatrix} v - \mu_v \\ f - \mu_f \end{pmatrix}$$

with means calculated from the non-amplification cluster $$B = \begin{pmatrix} v - \mu_v \\ f - \mu_f \end{pmatrix}$$

with means calculated from the wild-type positive cluster $\Sigma$ is the covariance matrix $$\begin{pmatrix} \text{var}(f) & \text{cov}(f, v) \\ \text{cov}(f, v) & \text{var}(f) \end{pmatrix}$$

with $\Sigma_A$ calculated from the non-amplification cluster and $\Sigma_B$ calculated from the wild-type positive cluster respectively.
p(v,f)=max(p1,p2)

This analysis can further be generalized to the case where only the non-amplification cluster exists (non-template control). For instance, 2D Gaussian modeling can be performed for the single cluster, and a subsequent probability, similar to $p_1$ discussed above, may be calculated for the single cluster. Because two probabilities are not calculated, the max( ) function is not performed.

In a sample run, a set of 42 TaqMan® assays may be chosen with 4 replicate runs of the wild-type control. Positive controls at 1 to 10% titration of the mutant alleles to fixed concentration of the wild-type allele may also be run for these assays. Based upon this data, in some embodiments, a threshold of −200 on log(p) may be chosen to identify a true false positive distinct from the scatter at the periphery of the wildtype cluster.

Figure 13A:
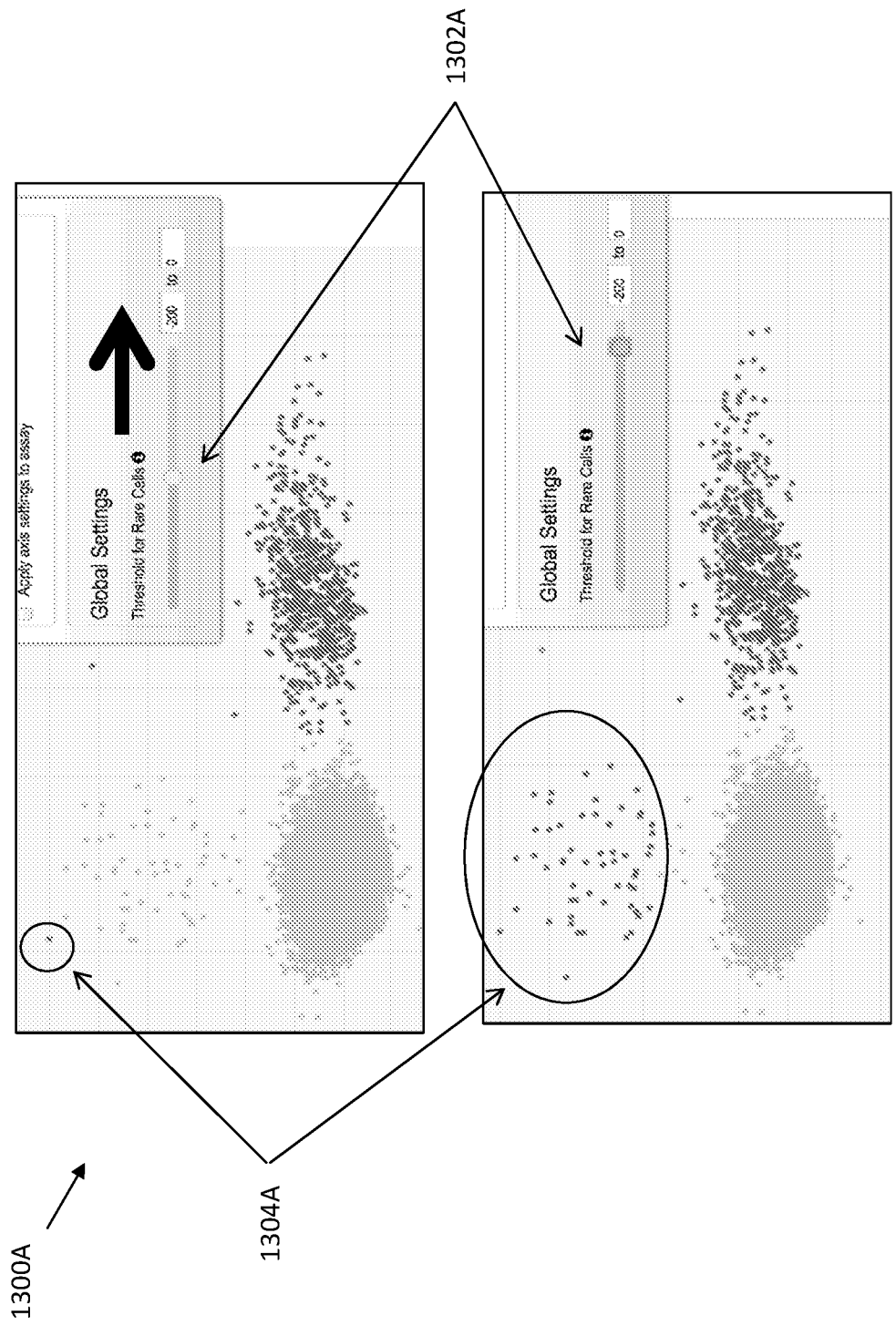
FIGS. 13A, 13B, 13C, and 13D illustrate exemplary graphical user interfaces with a scatter plot and an adjustable widget that may increase or decrease a threshold value used to make calls for data points according to various embodiments.
Figure 13B:
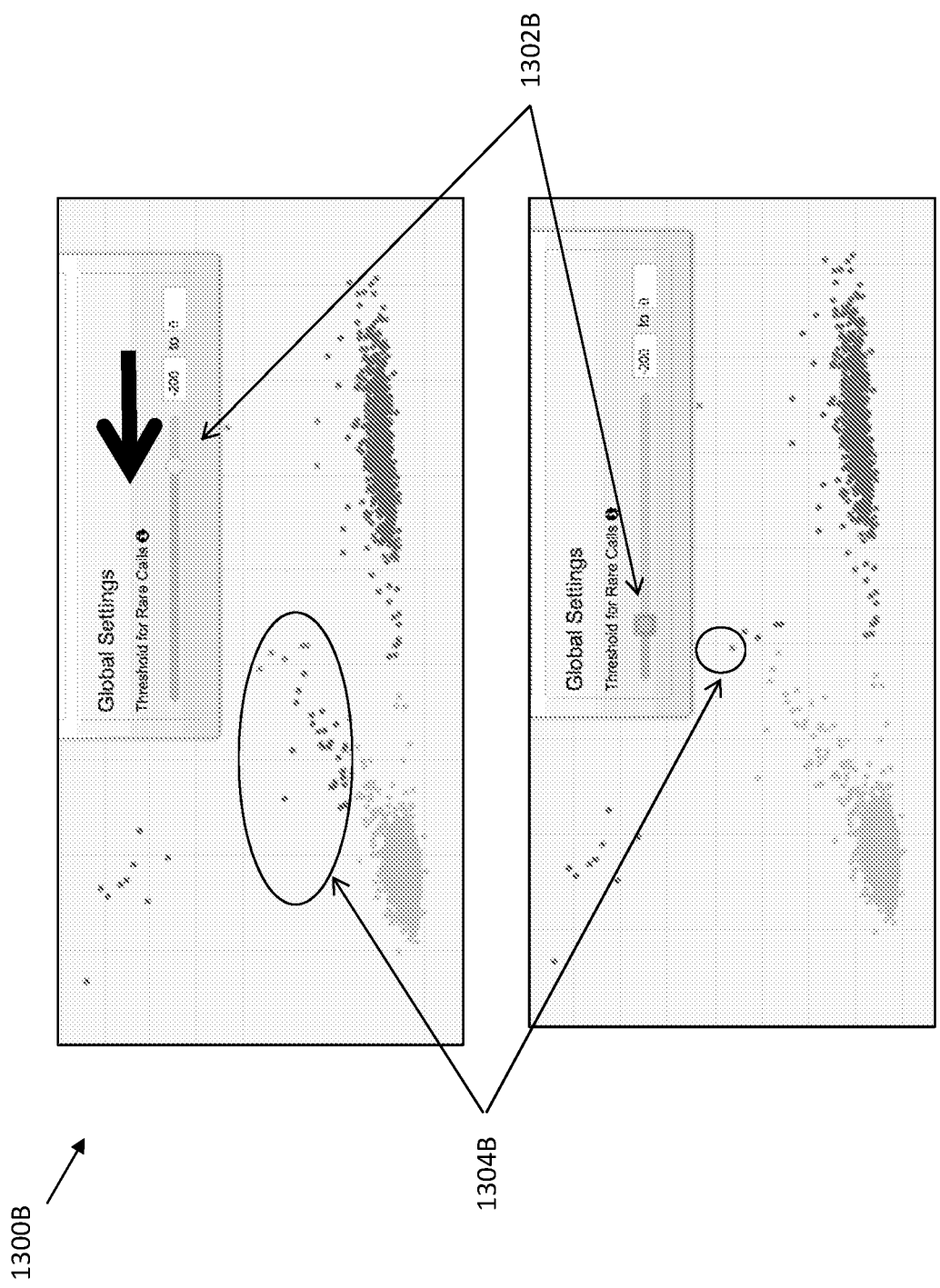

In some embodiments, the threshold used to identify a true false positive (e.g., to identify or call a rare data point) may be adjusted. For example, FIGS. 13A and 13B illustrate exemplary GUIs with a scatter plot and an adjustable widget that may increase or decrease the threshold value used to make calls for data points. In some embodiments, Method B, as described herein, may be used to identify clusters (e.g., a non-amplification cluster and a wild-type cluster) and calculate probabilities about whether particular data points belong to at least one of these clusters. In this example, the adjustable threshold may comprise log(p), as further described herein. When a threshold log(p) value is selected, data points with a probability outside the threshold may be called as true false positives (e.g., rare data points) while data points with a probability within the threshold may be called along with the clustered data points, such as one of non-amplifying or wild-type.

With reference to FIG. 13A, GUI 1300A illustrates an increase in the threshold used to call rare data points. For example, widget 1302A may comprise a slider that a user may manipulate to select a value for the threshold. While a slider is illustrated, any other suitable user interface element may be implemented. In the illustrated example, the slider is manipulated such that the threshold value increases, thus increasing the number of data points called as rare in the corresponding scatter plot. For instance, in this embodiment, because the threshold value comprises log(p) and ranges between "−200" and "0", an increase to the threshold value would reduce the calculated probability required for a particular data point to be called as rare. Changes to the data calls based on adjustments made to the threshold may also be displayed temporally (e.g., in real-time or near real-time) to the adjustment. For example, data points 1304A illustrate such a change to data calls, as prior to the adjustment to the threshold a small number of data points are called as rare and after the adjustment to the threshold the number of data points called as rare increases. In some embodiments, the changes to calls for particular data points may be illustrated based on a change in predetermined colors associated with data calls. For example, based on a received adjustment to the threshold from the user via slider 1302A, in real-time (or near real-time) calls may be changed for impacted data points, and the color of these data points may be changed to the color associated with the updated call.

GUI 1300B is similar to GUI 1300A, however a decrease in the threshold used to call rare data points is illustrated. For example, widget 1302B may also comprise a slider that a user may manipulate to select a value for the threshold. In the illustrated example, the slider is manipulated such that the threshold value decreases, thus decreasing the number of data points called as rare in the corresponding scatter plot. For instance, in this embodiment, because the threshold value comprises log(p) and ranges between "−200" and "0", a decrease to the threshold value would increase the calculated probability required for a particular data point to be called as rare. Data points 1304B illustrate this change, as prior to the adjustment to the threshold a large number of data points are called as rare and after the adjustment to the threshold the number of data points called as rare decreases.

Figure 13C:
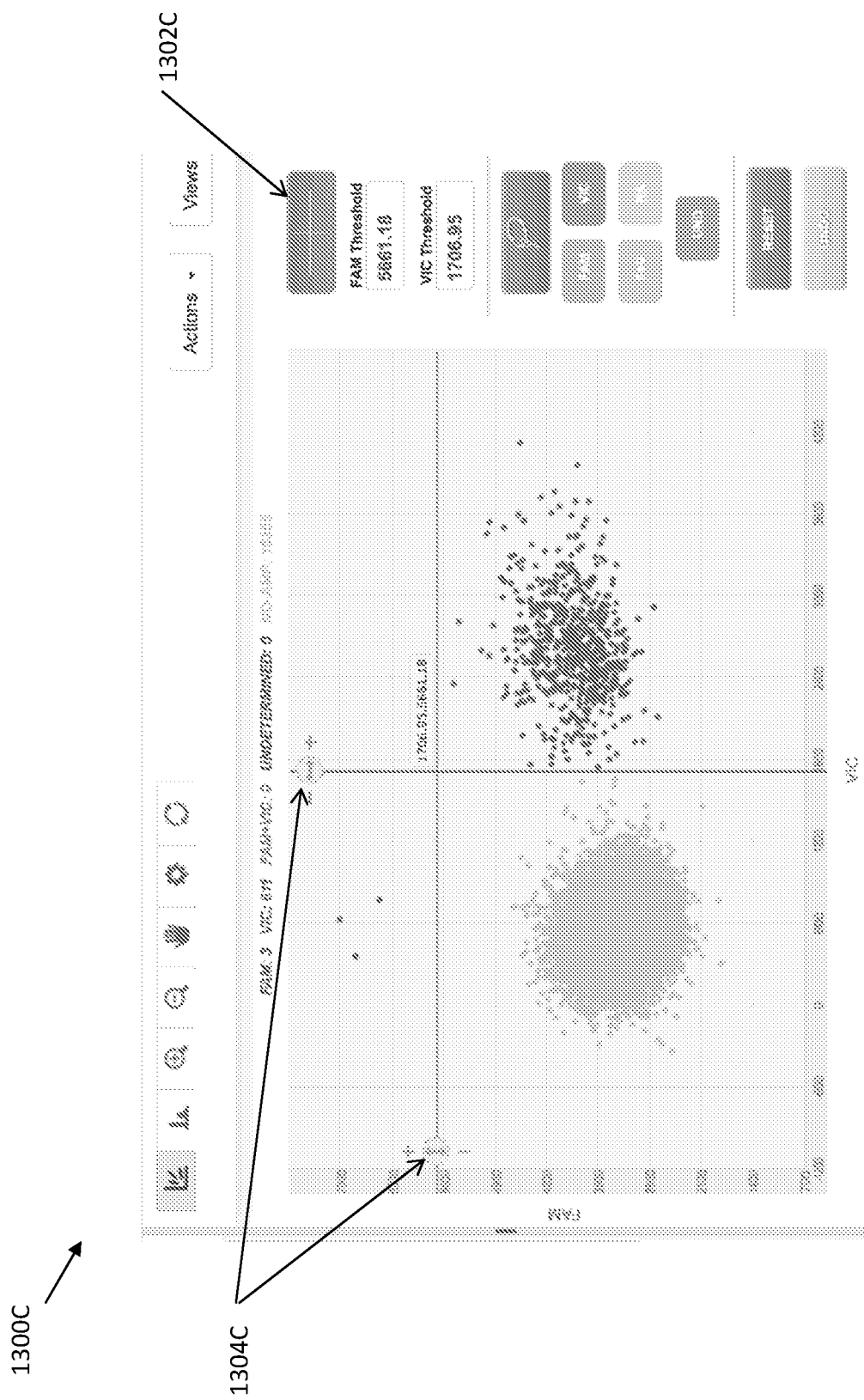
Figure 13D:
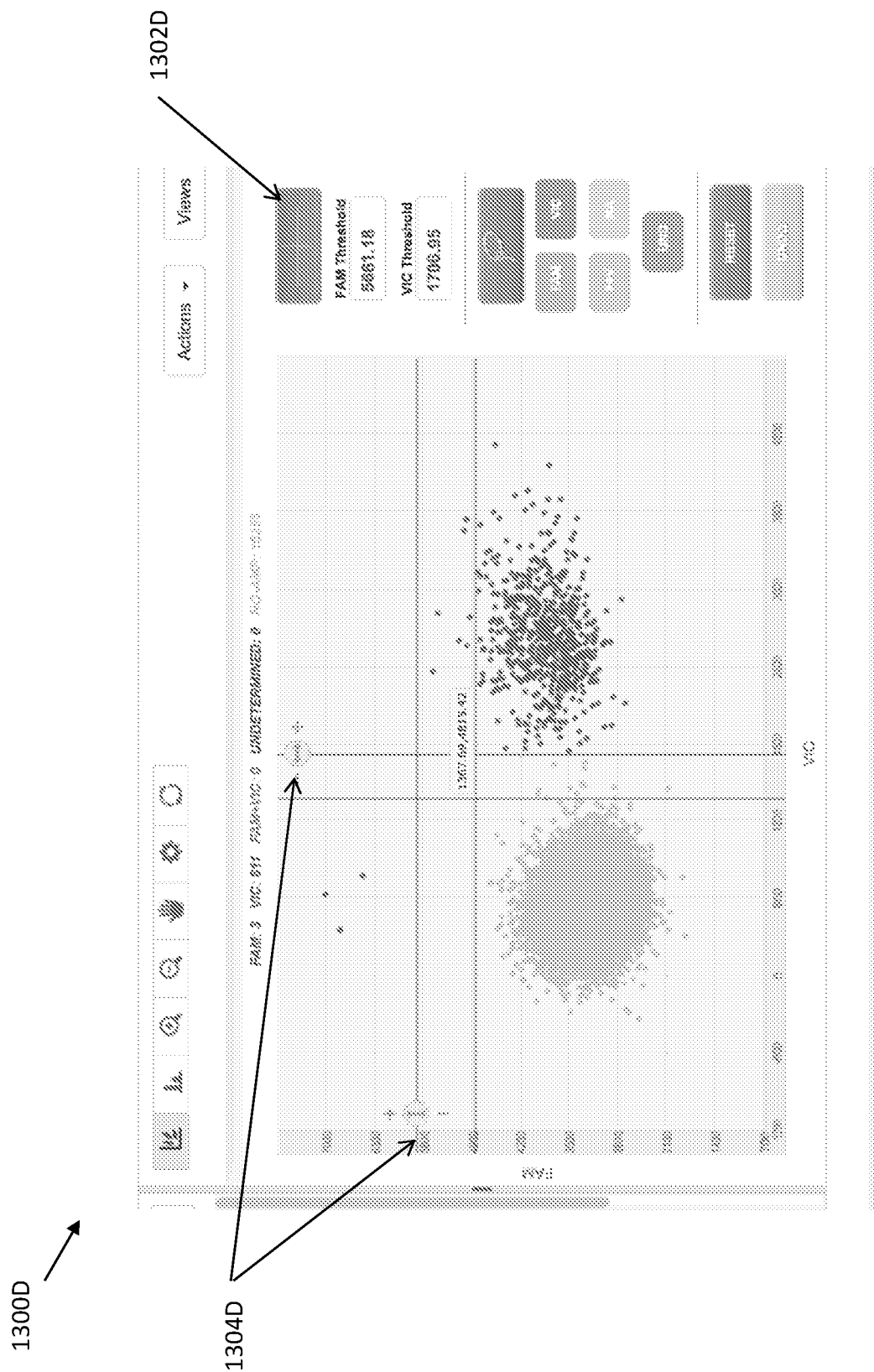

While FIGS. 13A and 13B illustrate an adjustable threshold related to Method B, discussed herein, adjustable thresholds may also be implemented for Method A, and any other suitable signal level based method for calling data points. For example, FIGS. 13C and 13D illustrate exemplary GUIs with a scatter plot and an adjustable widget that may increase or decrease the threshold value used to make calls for data points. With reference to FIG. 13C, GUI 1300C displays a scatter plot with button 1302C and adjustable threshold widgets 1304C. When a user clicks or otherwise actuates button 1302C, the crosshairs (e.g., intersecting lines) that correspond to the threshold values shown on the scatter plot may be displayed. In some examples, a threshold for each dimension of the scatter plot may be utilized (e.g., one for the x-axis and one for the y-axis). In the illustrated example, fluorescence results for two dyes are plotted, and thus each threshold value may correspond to one of the dyes.

In an example, widgets 1304C may be used to change the corresponding threshold values. For instance, the widgets may be clicked and dragged, or the "+" and "−" buttons on the threshold may be clicked or otherwise actuated to move the thresholds. FIG. 13D illustrates the thresholds after they have been adjusted by a user. GUI 1300D displays a scatter plot with button 1302D and adjustable threshold widgets 1304D. As illustrated, the displayed thresholds (e.g., lines on the scatter plot) show the pre-adjustment threshold values and the post-adjustment thresholds values. In some embodiments, the adjusted threshold values may then be used to make data point calls, as described herein. In some embodiments, the scatter plot displayed may comprises data from multiple reactions devices or sets of reactions sites (e.g., multiple chips). Accordingly, thresholds may be adjusted in view of data visualizations that provide an enhanced view of the generated data.

Various embodiments that implement such an adjustable threshold may provide a number of benefits to the user. For instance, because the threshold can be adjusted and the impact on data calls may be displayed on the corresponding scatter plot in real-time (or near real-time), a user may be provided the highly relevant information such that an accurate threshold may be selected.

Further, the clustering and probability calculations disclosed herein with reference to Method B enable more accurate automatic calls for rare data points. When Method B is combined with the adjustable threshold, a user may rely on an objective metric to call rare data points rather than relying on subjective (e.g., manual) user selection for individual data points. In addition, in some embodiments the adjustable threshold can be used for each data point generated by a given chip (or generated by a plurality of chips), or in other words, the adjustable threshold may be global. With such a global adjustable threshold, a user can rely on an objective and consistent criteria for automatically calling each rare data point on a given chip, and in some embodiments from chip to chip.

Figure 14:
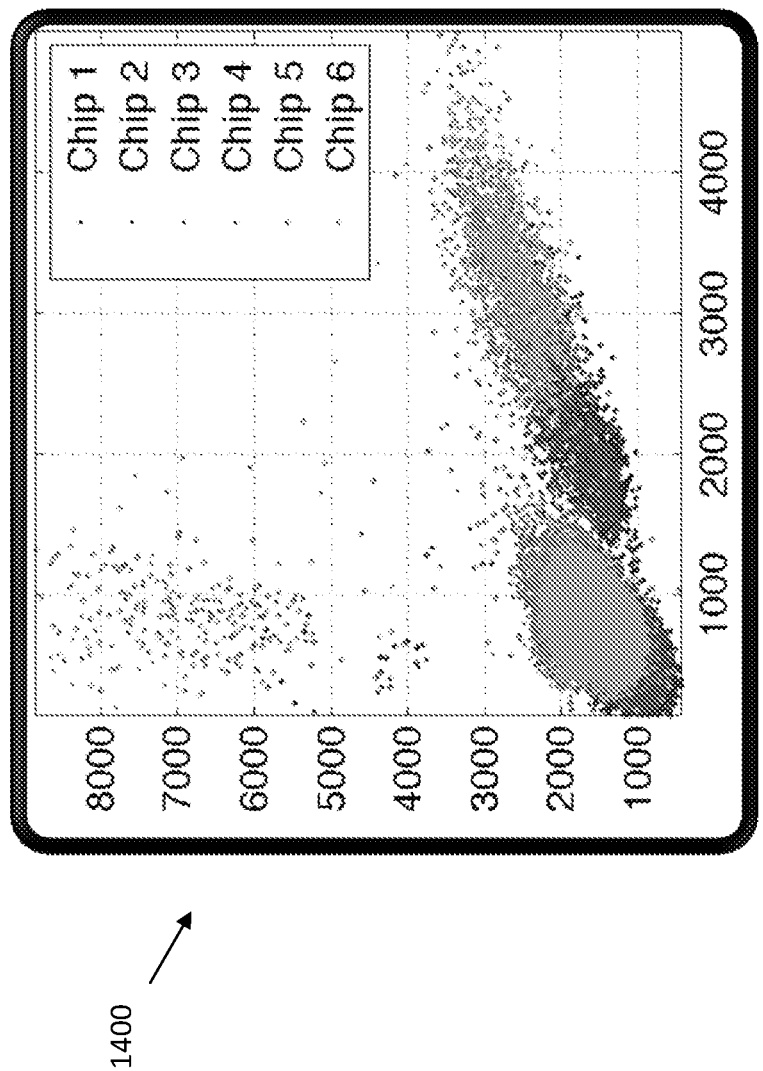
FIG. 14 illustrates an exemplary graphical user interface with a scatter plot that displays data generated from a plurality of chips according to various embodiments.

FIG. 14 illustrates an exemplary GUI 1400 with a scatter plot that displays data generated from a plurality of chips. In the illustrated example, if manual calls were required (e.g., using Method A as described above) variations between call decisions would fail to accurately identify rare data points and further fail to consistently identify rare data points with some objective criteria. As noted above, Method A is particularly susceptible to inter-run variation. On the other hand, in certain embodiments where Method B and the adjustable threshold are utilized, the accuracy of the rare calls is enhanced and the user can have confidence in the consistency between the calls for any given chip because these calls are based on a global threshold (e.g., an objective criteria). Since a global threshold can be used, the risks caused by inter-run variation that are particularly problematic with Method A may be mitigated.

In addition, because rare target calls are few in number, accuracy in such calls has a large impact on quantification results. Accordingly, the described benefits of Method B and the adjustable global threshold can, in certain embodiments and in certain circumstances, substantially improve the quantification results of rare targets. For instance, in a performed test, 67 rare mutation assays were tested using validation run data. For each assay, 10 reactions devices (e.g., chips) were used for testing. Of the 670 reaction devices, 128 exhibited accuracy issues with automatic calling using conventional methods (e.g., Method A). However, when using embodiments related to Method B described herein, the 128 reactions devices no longer exhibited the accuracy issues. Accordingly, in the reaction device space, a 19% improvement was observed. Further, 26 out of the 67 assays test showed accuracy improvement, or 39%. In a similar context that used assays with expected mono-modal results, 65 reaction devices out of 128 exhibited accuracy issues when using conventional methods. Again, when using embodiments related to Method B described herein, the 65 reaction devices no longer exhibited the accuracy issues. Accordingly, in the reaction device space, a 24% improvement was observed.

In various described embodiments, Method B may be used to analyze results based on digital PCR amplification. In other embodiments, Method B may also be used to analyze results from quantitative PCR amplification (qPCR). In qPCR, amplification of the target nucleic acid may be detected in real-time during the amplification process (e.g., at different cycles during a thermal cycling process) such that the initial and/or amplified target nucleic acid may be quantified. For example, an indicator of amplification, such as fluorescence, may be used in connection with qPCR. Dyes, such as a SYBR® dye or Taqman® florigenic probes, may be leveraged during PCR and amplification of the target nucleic acid may be detected based on the fluorescence exhibited by a reaction volume. In some embodiments, qPCR results may also include expected clusters, and thus the data analysis and quantification may derive benefits similar to those discussed above from the calculated probabilities used in Method B to automatically call data points. For instance, for qPCR reactions that leverage genotyping assays, we can expect results similar to those described here for dPCR. This data resemblance can also be true for qPCR reactions designed to amplify a rare target. In some embodiments, an adjustable global threshold, as described above, may also be used to configure the data calls and more accurate quantify the results on the qPCR reactions.

Figure 15:
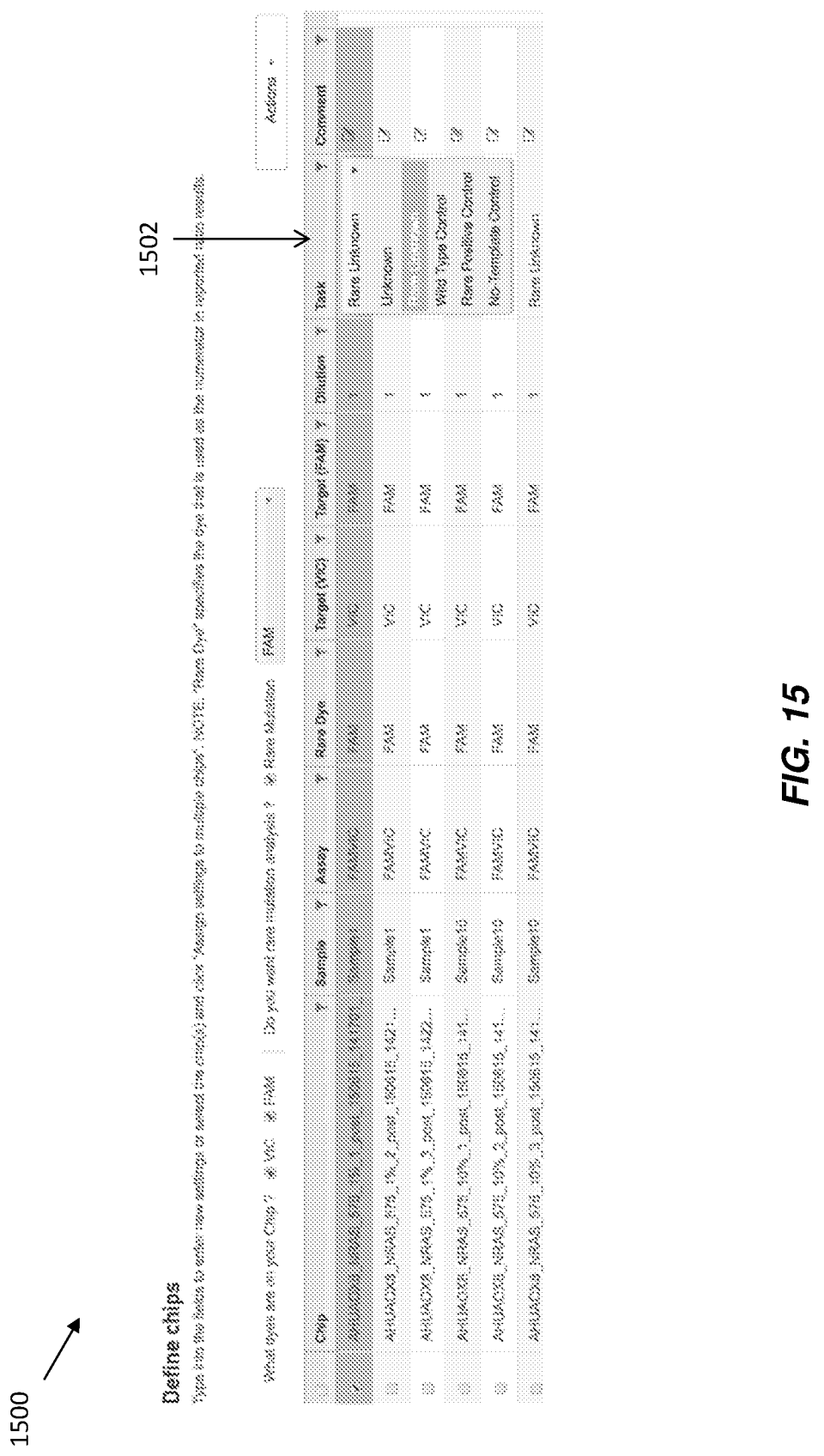

In an embodiment, when performing an analysis of PCR amplification, as described herein, for data generated from a chip, or a plurality of chips, a user may follow a particular sequence. FIG. 15 illustrates a GUI 1500 that displays a dashboard for configuring a rare mutation analysis. For instance, when performing a rare mutation analysis, various chips may perform tasks, where a chip can be associated with the tasks rare unknown (RUN), wild type control (WTC), rare positive control (RPC), and no-template control (NTC), as shown in drop down menu 1502. Here, the tasks association for a given chip depends on the target nucleic acid and assay used to perform the amplification. For instance, a chip configuration designed to amplify wild type target nucleic acids (without a rare target nucleic acid) may be designated with a WTC task. The RPC task and NTC task may be similarly associated with chips with amplification configurations corresponding to these tasks. In some embodiments, the RUN task may be associated with a chip designed to amplify both the wild-type target nucleic acid and the rare target nucleic acid. In some embodiments, predetermined dyes or probes may be associated with each of the wild type target nucleic acid and the rare target nucleic acid. In the illustrated example, FAM™ is associated with the rare target while VIC® is associated with the wild type target.

Figure 16:
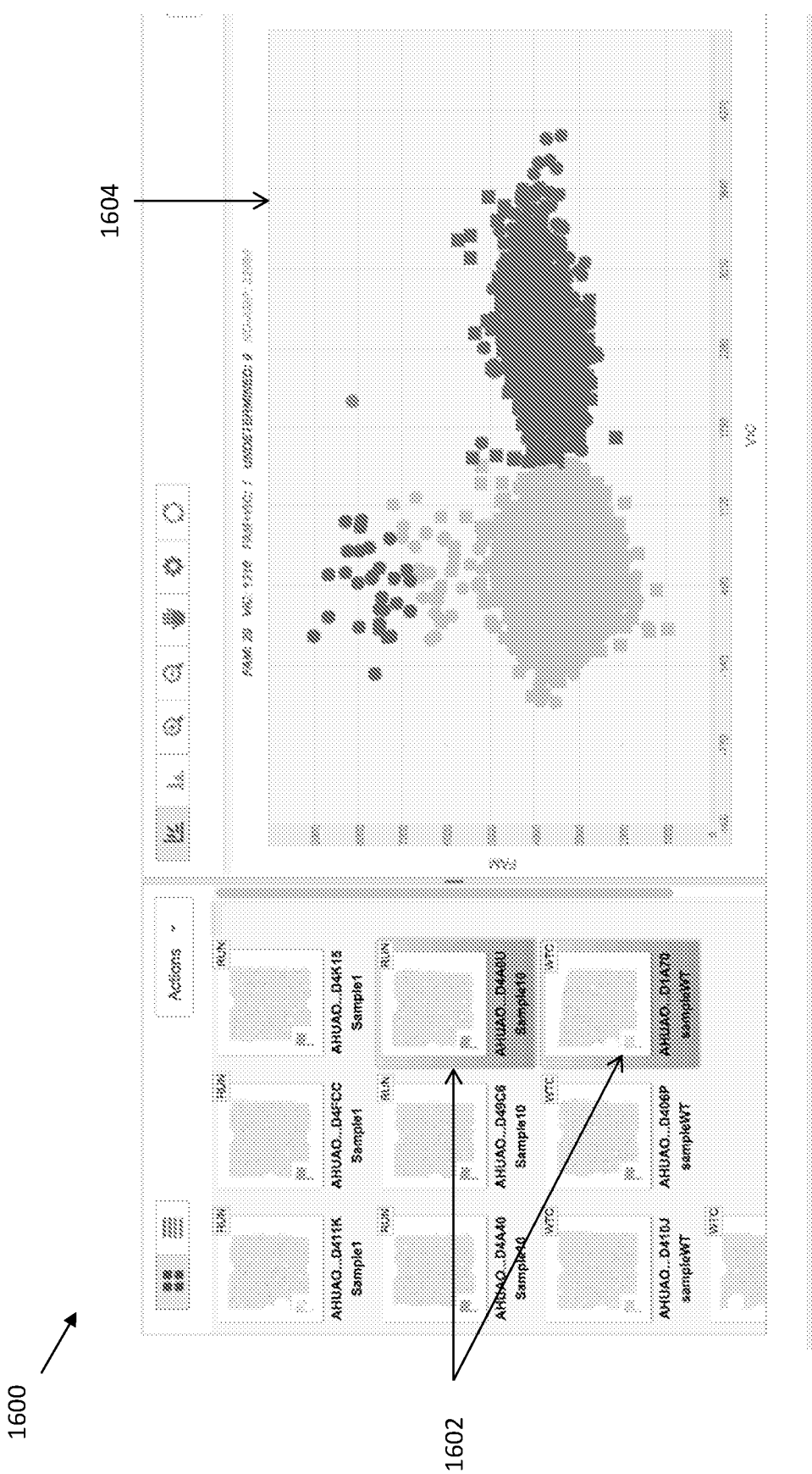
FIG. 16 illustrates a graphical user interface displaying data generated from a two chips associated with different tasks on a scatter plot according to various embodiments.

In an embodiment, data generated from multiple chips may be displayed in a single scatter plot. FIG. 16 illustrates data generated from a chip associated with a RUN task and a chip associated with a WTC task together on a scatter plot. For instance, thumbnails 1602 corresponding to the RUN associated chip and the WTC associated chip are selected, and the corresponding data generated from these chips is displayed on scatter plot 1604. Data generated from a control chip (such as the WTC associated chip) may be displayed as square data points to enable ease of source identification to a user viewing the data visualization.

In an embodiment, when a chip is associated with a RUN, WTC, or RPC task, Method B, as described herein, may be used to perform the analysis for data generated from these chips. For instance, based on the task association, it may be expected that one or more data point clusters (e.g., wild type cluster and/or non-amplification cluster) may be present, and thus it may be determined that the quantification calculation would benefit from the clustering and probability calculations used by Method B. For WTC associated chips, the rare data point calls (that do not belong with main cluster), are designed as false positives. For the RUN and RPC associated chips, the rare data points calls (that do not belong with main cluster), are used for quantifying the rare targets. In some embodiments, if a chip is associated with NTC task, the presence of one non-amplification cluster is expected. Here, data points not belonging with this cluster are interpreted as false positives. Based on the rare data points called and the corresponding designations (e.g., false positive or presence of rare target), the rare target may be quantified and the limit of detection (e.g., for a particular assay) may be calculated.

In some embodiments, once the chips are selected and associated with a task, one or more data analysis and visualizations may be performed, as described in various embodiments herein. For example, the Method B and the adjustable global threshold may be used to call data points generated by the selected chips. Based on the analysis and called data points, the wild-type and rare targets may be quantified. For example, based on the called data points for the selected chips, the tasks associated with the selected chips, and the significance for the data calls on a given chip (e.g., false positive, indicative of wild-type, or indicate of rare-target) the wild-type and rare targets may be quantified.

Figure 17:
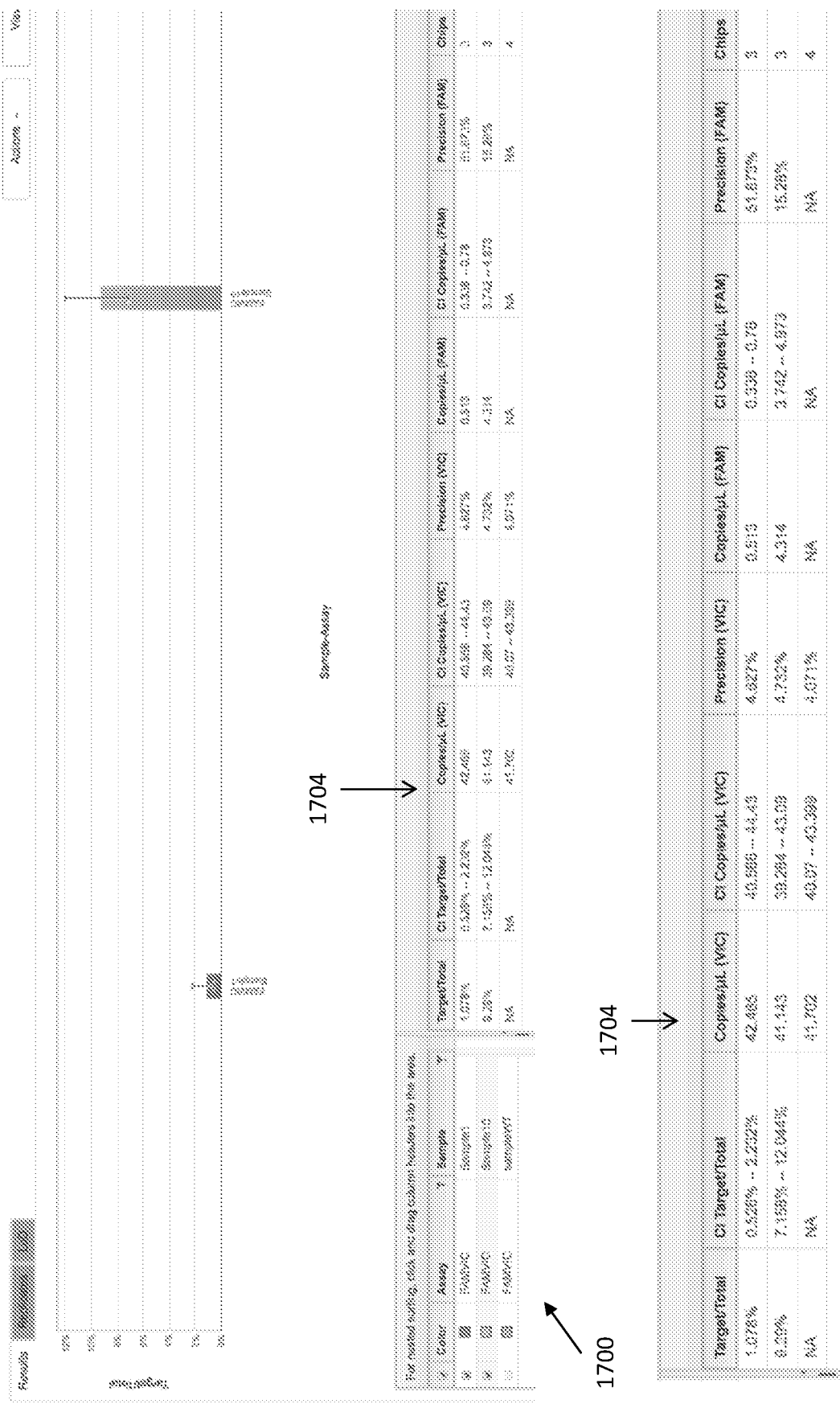
FIG. 17 illustrates an interface that display quantification results for a PCR reaction according to various embodiments.

FIG. 17 illustrates an interface that display quantification results for a PCR reaction. GUI 1700 includes table 1704 that shows a number of values related to rare target quantification. For instance, the first row of table 1704 shows quantification values of a rare target on 3 chips, as shown in the last column of the table. The columns of table 1704 represent: Target/Total, or ratio of rare target replicates as a percentage of total wild-type replicates; CI Target/Total, or the confidence interval for the Target/Total value; Copies/µL (VIC) and Copies/µL (FAM), or concentration of the targets for the VIC® and FAM™ dyes, respectively; CI Copies/pt (VIC) and CI Copies/pt (FAM), or confidence intervals for the concentration of the targets for the VIC® and FAM™ dyes, respectively; and Precision (VIC) and Precision (FAM), or how reproducible these values are given the CI values. Such quantification numbers can be used in a number of downstream applications, such as genotyping, disease screening, treatment verification and tracking, and a number of other applications.

Figure 18:
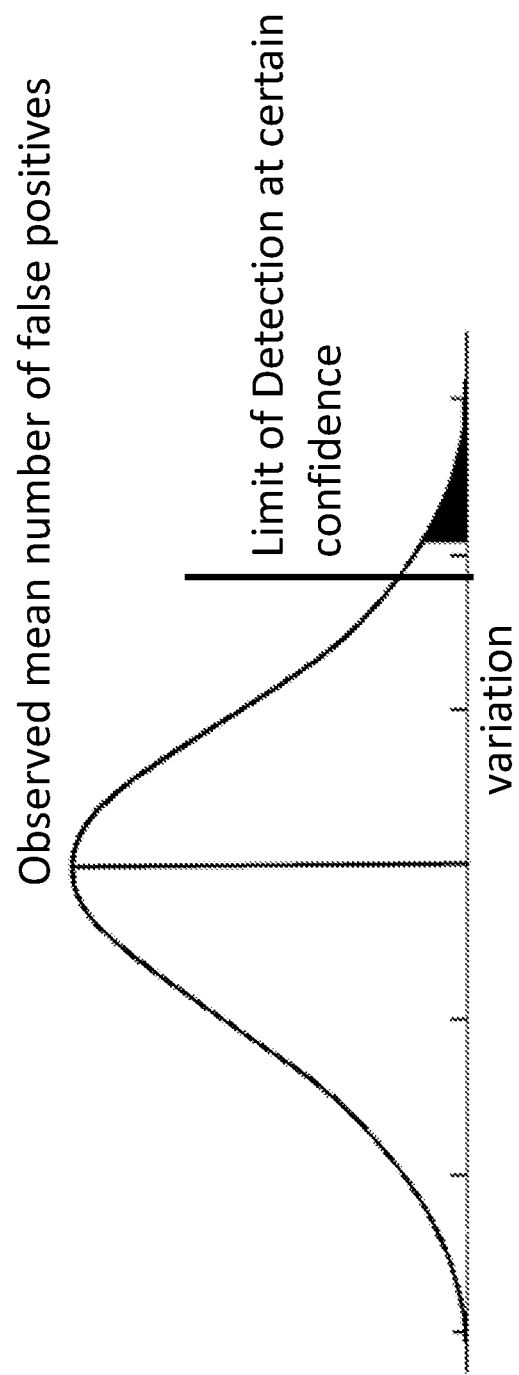
FIG. 18 illustrates a graph that displays the observed mean number of false positives and a limit of detection given a confidence according to various embodiments.

In some embodiments, the data generated from the chips and subsequent analysis may be used to determine a lowest limit of detection (LoD). FIG. 18 illustrates a graph that shows the observed mean number of false positives and subsequently shows a limit of detection given a predetermined confidence. In some embodiments, the LoD may be calculated based on the equation LoD=mean false positive+ (2× standard deviation). Here, the mean false positive may be normalized. For instance, once the number of false positives for the $i^{th}$ run is available, it MAY BE normalized by the wild-type load per equation 2 (from Coren A. Milbury, Qun Zhong, Jesse Lin, Miguel Williams, Jeff Olson, Darren R. Link, Brian Hutchison. "Determining the lower limits of detection of digital PCR assays for cancer-related gene mutations." Biomolecular Detection and Quantification. Volume 1, Issue 1. September 2014, Pages 8-22).

$$\text{Normalized \#False } Positive_i = \left( \frac{1}{k} \sum_{run\#i=1}^{k} \frac{\gamma^i_{mutant}}{\gamma^i_{wild-type}} \right) \times \gamma^i_{wild-type} \times N_i$$

Figure 19:
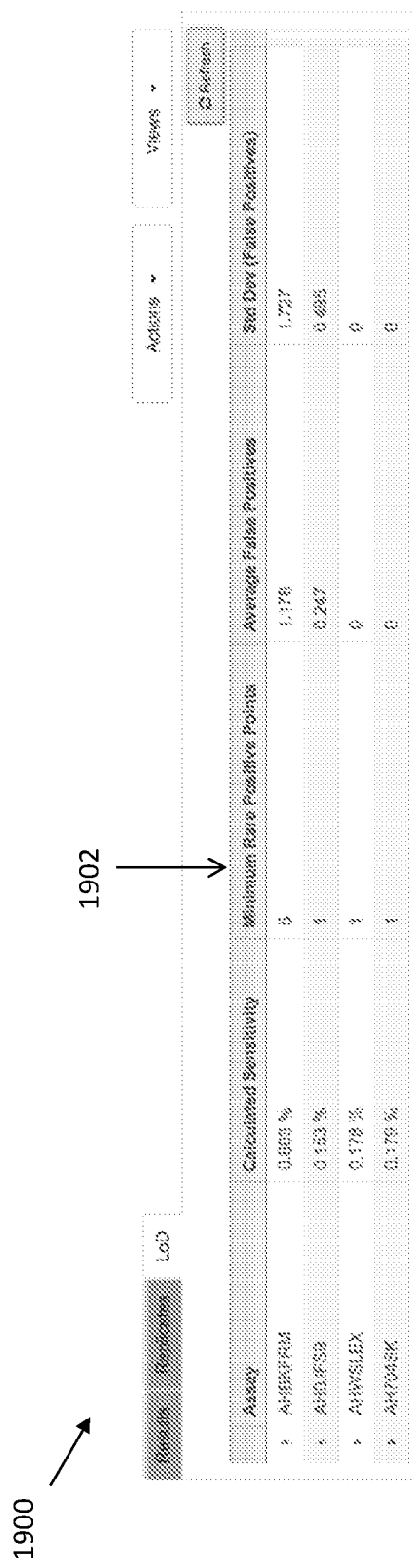
FIG. 19 illustrates a graphical user interface that displays limit of detection data for particular assays according to various embodiments.

FIG. 19 illustrates GUI 1900 that displays limit of detection data for particular assays. In some embodiments, based on a number of runs for a particular assay (e.g., using chips associated with control tasks or other tasks for quantifying false positives) an average false positives and a standard deviation for false positives may be calculated for the given assay. For example, in the illustrated example, one of the listed assays comprises a value of "5" in the minimum rare positive points column, or the LoD value. Considering the above equation, the LoD value of "5" may be confirmed by evaluating (1.178+(2×1.727)) and rounding up. In other embodiments, the value may be rounded in any suitable manner.

While the exemplary LoD calculation is performed herein use mean false positives and standard deviation values, any other suitable methodology for calculating LoD may be implemented. For example, the occurrence and distribution of false positives may be modeled using other suitable techniques and an LoD value may be calculated using the results from these techniques at a certain level of confidence.

In some embodiments, the LoD values calculated may use Method B to determine false positives. For example, based on the chip and the particular task associated with the chip, false positives may be determined using Method B (e.g., the clustering and probability method). Further, some embodiments may also utilize the adjustable global threshold described herein. Because, the false positive data used to calculated the LoD may benefit from the enhancements of accuracy and consistency described herein, various embodiments presented may also provide LoD values with enhanced accuracy and consistency.

Known alternatives to the embodiments of LoD calculations described herein may comprise physical titration tests to iteratively determine the limit at which such detection can occur. However, such tests can be both time consuming and costly.

In addition, the various embodiments may provide additional benefits to a number of downstream applications of the technological processes described herein. For instance, quantification of a rare target nucleic acids may be implemented when performing genetic testing for screening of a plurality of diseases. In addition, when medical practitioners treat a disease, such rare type quantification tests may be used to monitor the progression of treatment. The improvements in accuracy, consistency, and sensitivity (due to improvements in LoD calculations) may be used to enhance such screening processes and medical treatment.

While some of the data visualization and data analysis embodiments described above reference a particular reaction device, such as a chip, any suitable reaction device capable of performing PCR amplification may be implemented. For example, as an alternative to carrying out nucleic acid amplification monitoring in a stationary sample, the sample may be caused to flow through a channel or chamber of a microfluidic device and as it flows it may be subjected consecutively to different temperatures whereby thermo-cycling is achieved. Further, as an alternative to reaction chambers, through-holes, or microwells, droplets may be formed and used to perform low volume PCR amplification. The data visualization techniques described herein, as well as the data analysis techniques, may be applied to PCR results obtain from any suitable reaction device or system.

In some embodiments, a method, system, and/or a non-transitory computer-readable storage medium for generating a data visualization may be presented. Graphical images representing a plurality of sets of reaction sites may be displayed to the user. At least one of the graphical images representing the sets of reaction sites may be selected by the user. A representation of detected data from the at least one selected set of reaction sites may be generated. And an indication of data quality value for the detected data may be displayed along with the representation of detected data.

In some embodiments, the indication of data quality value is color. In some embodiments, the detected data is florescence emission data detected from the set of reaction sites. In some embodiments, the set of reaction sites comprises 20,000 or 40,000 reaction sites. In some embodiments, the representation of detected data is a display selected from the group consisting of a heat map, a cluster or scatter plot, a histogram, and combinations thereof. In some embodiments, the graphical images representing the sets of reaction sites are thumbnail displays. In some embodiments, the heat map display replaces the graphical images representing the plurality of sets of reaction sites. In some embodiments, the data applied to at least two of the cluster or scatter plot display, the heat map display, the graphical images representing the sets of reaction sites, and histogram display, are synchronized such that changes to one display are reflected on the synchronized display. In some embodiments, the displays of least two of the cluster or scatter plot display, the heat map display, the graphical images representing the sets of reaction sites, and histogram display, are viewable on a single display.

In some embodiments, the user may further select at least one data point of the detected data on the cluster or scatter plot. The at least one data point of the detected data may be labeled to differentiate the at least one data points from the remaining data points of the detected data. The corresponding at least one data point on a co-located heat map may be labeled, wherein the corresponding at least one data point is differentiated from the remaining data points of the detected data. In some embodiments, the selected at least one data point is labeled with a different color from the remaining data points of the detected data. In some embodiments, the heat map display is provided with a zoom feature to better analyze specifically selected points on the heat map.

In some embodiments, based on input from a user, a quality value threshold may be selected based on user analysis of the at least two representations of detected data. Updated representations may be generated of the at least two representations of detected data analyzed, wherein the selected quality value threshold is displayed on the at least two representations of detected data. An indication of data quality value for the detected data meeting the quality value threshold may be displayed.

In some embodiments, a data manipulation tool may be provided comprising at least one filtering option, wherein the tool automatically selects at least one of the representations of the sets of reaction sites based on input from a user selecting the filtering option. In some embodiments, the at least one filtering option is grouping by replicate or grouping by assay.

In some embodiments, a method or system for visualizing data generated from one or more reaction devices, chips, or reaction sites may be provided. On a scatter plot, data points may be displayed indicative of results from nucleic amplification, wherein the nucleic acid amplification comprises a first target and a second target and the data points are designated as being indicative of amplification of the first target, the second target, both targets, or neither target. In response to user input, an adjustable threshold may be varied used to designate the data points. And, in response to the varying, designations and a display of the designations may be altered for one or more of the data points whose designation is changed based on the varied threshold. In some embodiments, an indicator may be displayed indicative of the designations for the data points, the indicator comprising a predetermined color. And, in response to the varying, the displayed indicator may be altered for the data points in accordance with the altered designations.

In some embodiments, for a plurality of data points on the graph, one or more clusters of data points may be identified, wherein each cluster is associated with one of the designations. In some embodiments, the adjustable threshold comprises a probability threshold such that, for a given data point, when a calculated probability that the data point belongs to the one or more clusters is within the threshold, the data point is designated along with the respective cluster, and when the calculated probability is not within the threshold, the data point is given a designation different from the designation of the respective cluster. In some embodiments, the data points correspond to data received from a plurality of reaction sites, a portion of the reaction sites hosting nucleic acid amplification. In some embodiments, that data points are based on fluorescence detected from the plurality of reaction sites in response to an amplification assay. In some embodiments, sets of reaction sites and corresponding data points are associated with one or more amplification assays such that the assays are designed to amplify one or both of the first and second target nucleic acids.

Figure 20:
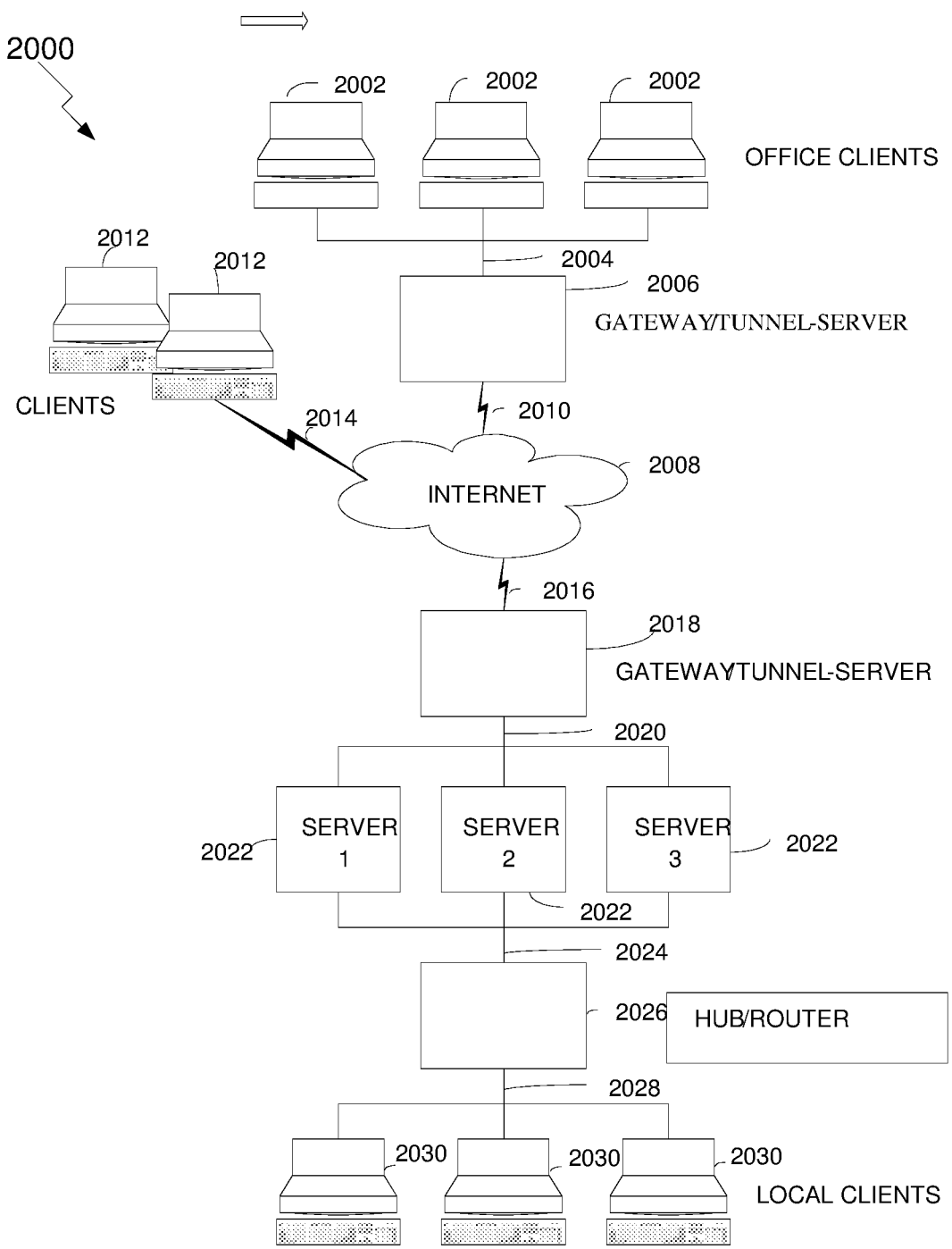
FIG. 20 illustrates an exemplary distributed network system according to various embodiments.

In some embodiments, for at least one amplification assay, a limit of detection may be calculated for amplification of one of the first and second target nucleic acids, wherein the limit of detection is based on the designations for the data points and associations between sets of the data points and the at least one amplification assay. The limit of detection may then be displayed. In some embodiments, the first and second target nucleic acids comprise a nucleic acid corresponding to rare type allele and a nucleic acid corresponding to a wild-type allele FIG. 20 is a diagram illustrating an example system 2000 configured in accordance with one example embodiment. In system 2000, one or more servers 2022 can be configured to run the analysis applications for analyzing data sets produced by one or more devices or modalities 2040. The data included in the data sets can be stored in one or more storage devices 2050. Once the data sets have been uploaded to servers 2022, then a plurality of applications running on servers 2022 can be used to manipulate, analyze and visualize the data sets from anywhere. For example, local client devices 2030 can be used to access servers 2022, e.g., through a hub or router 2026. At the same time, the data can be accessed remotely through remote clients devices 2002, which are interfaced with servers 2022, e.g., via a gateway/hub/tunnel-server/etc. 2010, which is itself connected to the internet 2008 via some internet service provider (ISP) connection 2010, or remote client servers 2012, which are interfaced with servers 2022, e.g., via the internet 2008 and via an ISP connection 2014.

It should also be noted that devices 2040 can be directly interfaced with servers 2022, e.g., through the internet. In such embodiments, the collection application and functionality can reside on servers 2022, on devices 2040, or both. In other embodiments, devices 2040 can be interfaced with client devices 2002 or 2012. In such embodiments, the collection application or functionality can be included on client devices 2002 or 2012, devices 2040, or both.

Client devices 2002, 2012, and 2030 can be any kind of computing device that can be used to access servers 2022. As such, these devices can be laptop, desktop, or palmtop computers, terminals, mobile computing devices such as smartphones or tablets, etc. Servers 2022 can comprise one or more processors, servers, routers, co-processors, user interfaces, etc., whether co-located or located in different locations. In short, servers 2022 can comprise all of the resources, both hardware and software, needed to perform the functions described herein. A more detailed description of a computer system and the resources that can be used to implement the components illustrated in FIG. 20 is described above with respect to FIG. 1.

Those skilled in the art will appreciate that the features described above can be combined in various ways to form multiple variations of exemplary embodiments in accordance with the present disclosure, and that various modifications may be made to the configuration and methodology of the exemplary embodiments disclosed herein without departing from the scope of the present disclosure and claims. Those skilled in the art also will appreciate that various features disclosed with respect to one exemplary embodiment herein may be used in combination with other exemplary embodiments with appropriate modifications, even if such combinations are not explicitly disclosed herein.

What is claimed is:

1. A method for generating a data visualization, the method comprising:
simultaneously displaying, at a graphical user interface, a plurality of individually selectable graphical images, each individually selectable graphical image comprising a heat map representation of a set of detected data from reaction sites corresponding to a respective sample holder of a plurality of sample holders;

receiving from a user a selection of at least two graphical images of the plurality of individually selectable graphical images;

simultaneously displaying multiple representations of the sets of detected data from the reaction sites corresponding to the at least two graphical images selected by the user, the multiple representations comprising a heat map and a scatter plot;

displaying, along with the multiple representations of the sets of detected data, an indication of data quality for the detected data;

receiving from the user a selection of a data point from the scatter plot;

labeling the data point from the scatter plot in response to the selection of the data point by the user, the labeling of the data point from the scatter plot being sufficient to differentiate the data point from unselected data points of the scatter plot; and labeling at least one corresponding data point on the heat map data point corresponding to the data point from the scatter plot, the labeling of the data point of the heat map being sufficient to differentiate the data point from data points of the heat map not corresponding to selected data points of the scatter plot.

2. The method of claim 1, wherein the indication of data quality is a color.

3. The method of claim 1, wherein the detected data is fluorescent emission data.

4. The method of claim 3, wherein the fluorescent emission data is detected from each set of reaction sites.

5. The method of claim 4, wherein each set of reaction sites is at least 20,000 reaction sites or 40,000 reaction sites.

6. The method of claim 1, wherein the multiple representations further comprise a histogram.

7. The method of claim 1, wherein the graphical images are displayed as thumbnail displays.

8. The method of claim 1, wherein the heat map and the scatter plot are synchronized such that changes to one display of the heat map and the scatter plot are reflected on the other of the heat map and the scatter plot.

9. The method of claim 1, wherein the selected data point is labeled with a different color from unselected data points of the detected data.

10. The method of claim 1, wherein the heat map is provided with a zoom feature to analyze specifically selected points on the heat map.

11. The method of claim 1, further comprising providing a data manipulation tool comprising at least one filtering option, wherein the tool automatically selects one or more of the graphical images based on input from the user selecting the filtering option.

12. The method of any of claim 11, wherein the at least one filtering option comprises one or both of grouping by replicate and grouping by assay.

13. A system for generating a data visualization, the system comprising:
a processor; and
a memory encoded with instructions for performing a method according to claim 1.

14. A non-transitory computer-readable storage medium encoded with instructions, executable by a processor, the instructions comprising instructions for performing a method according to claim 1.

15. The method of claim 1, further comprising:
receiving a quality value threshold from a user, wherein the data quality of the detected data comprises data quality values corresponding to data points of the detected data;
generating updated representation based on the data quality values relative to the received quality value threshold; and
displaying the indication of data quality for the detected data based on the quality value threshold.

16. The method of claim 15 wherein the received quality value threshold is displayed on the graphical user interface.

17. The method of claim 15, wherein the quality value threshold comprises a probability threshold such that when a probability of a data point of the detected data is outside the probability threshold, the data point is considered a false positive, and when the probability is within the probability threshold, the data point is considered to be a true positive, the probability being a probability of the data point belonging to a cluster of data points of the scatter plot.

18. The method of claim 1, wherein the scatter plot comprises a plurality of clusters comprising one or more data points of the detected data.

19. The method of claim 18, wherein the data quality of the detected data comprises data quality values corresponding to data points of the detected data, each data quality value representing a probability of the data point of the detected data belonging to a cluster of the plurality of clusters.

20. The method of claim 1, wherein at least one of the at least two graphical images corresponds to a set of detected data from reaction sites of a sample holder used as for a control assay comprising one or more of a wild type control (WTC) assay, a rare positive control (RPC) assay, and a no template control (NTC) assay, and at least one of the at least two graphical images corresponds to a set of detected data from reaction sites of a sample holder used for a rare unknown (RUN) assay.

* * * * *